(12) United States Patent
Giese et al.

(10) Patent No.: US 9,314,397 B2
(45) Date of Patent: Apr. 19, 2016

(54) SYSTEMS AND METHODS FOR CONTROLLING TRANSDUCERS TO PROVIDE A VIBRACOUSTIC EXPERIENCE

(75) Inventors: Robert Giese, Sheboygan, WI (US); Glen Rauwerdink, Hingham, WI (US); Santosh Narasimhan, Port Washington, WI (US); Ken Lefeber, Plymouth, WI (US)

(73) Assignee: KOHLER CO., Kohler, WI (US)

( * ) Notice: Subject to any disclaimer, the term of this patent is extended or adjusted under 35 U.S.C. 154(b) by 1025 days.

(21) Appl. No.: 13/439,753

(22) Filed: Apr. 4, 2012

(65) Prior Publication Data

US 2013/0263370 A1 Oct. 10, 2013

(51) Int. Cl.
| | |
|---|---|
| A47K 3/00 | (2006.01) |
| A61H 23/02 | (2006.01) |
| A61H 33/00 | (2006.01) |
| A61H 9/00 | (2006.01) |
| A61N 5/06 | (2006.01) |

(52) U.S. Cl.
CPC ........ *A61H 23/0236* (2013.01); *A61H 33/6089* (2013.01); *A61N 5/0618* (2013.01); *A61H 9/0021* (2013.01); *A61H 33/6005* (2013.01); *A61H 2033/0054* (2013.01); *A61H 2033/0083* (2013.01); *A61H 2201/10* (2013.01); *A61H 2201/5007* (2013.01); *A61H 2201/5015* (2013.01); *A61H 2201/5046* (2013.01); *A61H 2201/5048* (2013.01); *A61N 2005/0663* (2013.01); *A61N 2005/0668* (2013.01); *Y10T 137/8593* (2015.04)

(58) Field of Classification Search
CPC ........... A61H 33/0091; A61H 33/0087; A61H 33/6089
USPC ....................................... 4/541.1–541.6, 559
See application file for complete search history.

(56) References Cited

U.S. PATENT DOCUMENTS

| | | | | |
|---|---|---|---|---|
| 3,585,991 A | * | 6/1971 | Balamuth | 601/157 |
| 4,797,958 A | * | 1/1989 | Guzzini | 4/541.2 |
| 5,422,519 A | * | 6/1995 | Russell | 307/104 |
| 6,453,484 B1 | * | 9/2002 | Pinciaro | 4/541.6 |
| 7,489,787 B2 | * | 2/2009 | Macey | 381/89 |
| 2009/0241253 A1 | | 10/2009 | Glasford et al. | |

FOREIGN PATENT DOCUMENTS

| | | |
|---|---|---|
| EP | 0935957 | 8/1999 |
| JP | H0315423 | 1/1991 |
| WO | WO 98/27923 | 7/1998 |

OTHER PUBLICATIONS

Extended European Search Report in Application No. EP13162221.9 mailed Nov. 7, 2013.

* cited by examiner

*Primary Examiner* — Huyen Le
(74) *Attorney, Agent, or Firm* — Foley & Lardner LLP

(57) ABSTRACT

This disclosure relates to a vibroacoustic water system. The water system includes a reservoir configured to contain water and comprising a wall. The water system further includes four transducers mounted against the wall of the reservoir. The four transducers are configured to receive an input signal and to generate vibrations within water contained in the reservoir by vibrating the wall of the reservoir. The four transducers are mounted in a configuration such that, when the wall is partitioned into four sections, only a single transducer is mounted against each section of the wall and no other transducers are mounted against the wall.

21 Claims, 26 Drawing Sheets

United States Patent US 9,314,397 B2

SYSTEMS AND METHODS FOR CONTROLLING TRANSDUCERS TO PROVIDE A VIBRACOUSTIC EXPERIENCE

BACKGROUND

The present disclosure relates generally to the field of bathroom fixtures. More specifically, various embodiments of the present disclosure relate to bathroom fixture systems configured to provide aural and/or vibratory stimulation and systems and methods for controlling such bathroom fixture systems.

Shower and bath fixtures vary widely in the features they provide. Many basic bath fixtures, for example, provide a bath tub or basin, a faucet for adding water to the tub and a drain for removing water, and few, if any, other features. Some consumers wish to purchase fixtures that have more advanced features that make taking a bath or shower more enjoyable and/or relaxing in addition to being merely functional. One such feature, for example, may include water jets in a bath tub configured to provide a tactile (e.g., massaging) stimulus for the user. Another feature may include devices (e.g., transducers) configured to generate sound to allow a user to listen to music, relaxing nature sounds, or some other manner of aural stimulus while showering or bathing.

SUMMARY

One embodiment of the disclosure relates to a water system that includes a reservoir configured to contain water and comprising a wall. The water system further includes four transducers mounted against the wall of the reservoir. The four transducers are configured to receive an input signal and to generate vibrations within water contained in the reservoir by vibrating the wall of the reservoir. The four transducers are mounted in a configuration such that, when the wall is partitioned into four sections, only a single transducer is mounted against each section of the wall and no other transducers are mounted against the wall.

Another embodiment relates to a bathing system that includes a tub configured to contain water and comprising a wall. The bathing system further includes four vibratory transducers mounted against the wall of the tub. The four transducers are configured to receive an input signal and to generate vibrations within water contained in the tub by vibrating the wall of the tub. The bathing system further includes a plurality of audio transducers mounted on the tub at positions above a maximum water level of the tub and configured to receive an input signal and generate an aural output using the tub. The bathing system further includes a control circuit configured to generate signals to drive both the vibratory transducers and the audio transducers. The four vibratory transducers are mounted in a configuration such that, when the wall is partitioned into four sections, only a single vibratory transducer is mounted against each section of the wall and no other transducers are mounted against the wall.

Another embodiment relates to a water system that consists of a reservoir configured to contain water and comprising a wall and four transducers mounted against the wall of the reservoir. The four transducers are configured to receive an input signal and to generate vibrations within water contained in the reservoir by vibrating the wall of the reservoir. The four transducers are mounted in a configuration such that, when the wall is partitioned into four sections, only a single transducer is mounted against each section of the wall and no other transducers are mounted against the wall.

Yet another embodiment of the disclosure relates to a user interface system for a vibroacoustic bath. The user interface system includes a resistive touchscreen device configured to display images and to receive touch input via a panel of the resistive touchscreen device. The resistive touchscreen device is configured to display at least one image for use in controlling the vibroacoustic bath. The resistive touchscreen is further configured to receive a user selection relating to the image. The user interface system also includes a control circuit configured to use the received user selection to determine output signals for driving a plurality of transducers of the vibroacoustic bath.

Another embodiment relates to a user interface device for use with a bath or shower system that includes a resistive touchscreen device configured to display images and to receive touch input via a panel of the resistive touchscreen device. The user interface device further includes a protective screen positioned in front of the panel of the resistive touchscreen device and configured to protect the panel and a housing comprising a front cover and a back cover, wherein the front cover and the back cover are welded together. The user interface device further includes an adhesive material deposited between the protective screen and the front cover of the housing and configured to prevent moisture from traveling between the protective screen and the front cover and into contact with the resistive touch screen device. The user interface device further includes at least one of a potting material and a gasket disposed between the housing and the resistive touchscreen device at a location proximate to a joint at which the front cover and the back cover are welded together. The at least one of the potting material and the gasket is configured to prevent moisture from traveling between the front cover and the back cover and into contact with the resistive touch screen device.

Yet another embodiment relates to a user experience system for a vibroacoustic bath. The user experience system includes a user interface device. The user interface device includes a resistive touchscreen device configured to display images and to receive touch input via a panel of the resistive touchscreen device. The user interface device further includes a protective screen positioned in front of the panel of the resistive touchscreen device and configured to protect the panel and a housing comprising a front cover and a back cover, wherein the front cover and the back cover are welded together. The user interface device further includes an adhesive material deposited between the protective screen and the front cover of the housing and configured to prevent moisture from traveling between the protective screen and the front cover and into contact with the resistive touch screen device. The user interface device further includes at least one of a potting material and a gasket disposed between the housing and the resistive touchscreen device at a location proximate to a joint at which the front cover and the back cover are welded together. The at least one of the potting material and the gasket is configured to prevent moisture from traveling between the front cover and the back cover and into contact with the resistive touch screen device. The user experience system further includes a plurality of transducers. A first subset of the transducers are configured to be positioned below a maximum water level of the vibroacoustic bath and are configured to generate vibrations within water contained in the vibroacoustic bath by vibrating a wall of the vibroacoustic bath. A second subset of the transducers are configured to be positioned above a maximum water level of the vibroacoustic bath and are configured to generate an aural output using the vibroacoustic bath. The user experience system further includes a control circuit configured to receive signals representing the touch input from the user interface device and to generate output signals to drive the transducers based on the touch input.

DETAILED DESCRIPTION

Figure 1:
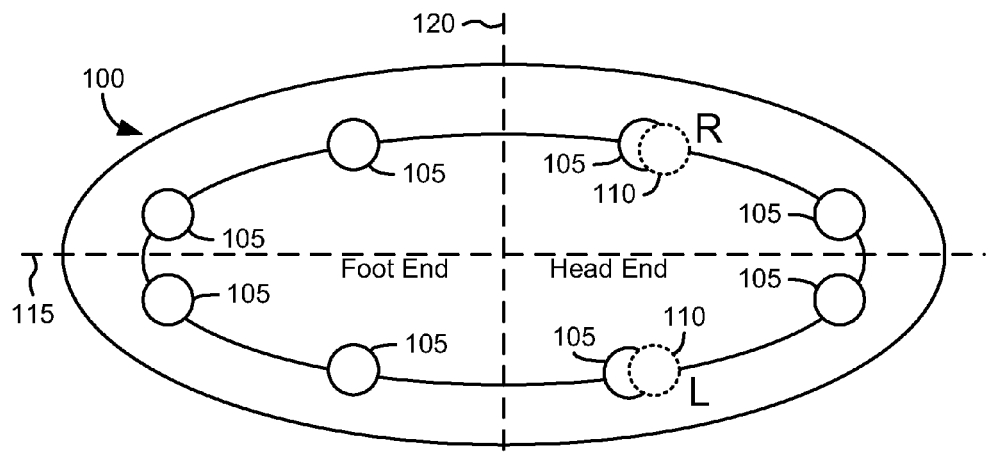
FIG. 1 is a simplified plan view of a bath tub illustrating a position of a plurality of transducers according to an exemplary embodiment.

Before turning to the figures, which illustrate the exemplary embodiments in detail, it should be understood that the application is not limited to the details or methodology set forth in the description or illustrated in the figures. It should also be understood that the terminology is for the purpose of description only and should not be regarded as limiting.

Referring generally to the figures, systems and methods for providing an enhanced user experience in connection with a bathroom fixture (e.g., a shower or bath tub) using tactile, aural, and/or visual stimuli are described according to various exemplary embodiments. In some embodiments, a bath tub or other plumbing fixture may be equipped with transducers that generate particular types of output based on input signals. Some of the transducers may be positioned below a top water level of the bath tub and configured to generate vibrations in the water by vibrating the reservoir of the tub at particular frequencies. Some transducers may be positioned above the top water level and configured to generate aural output, such as music or relaxing sounds (e.g., nature sounds).

In some embodiments, a user experience system for a vibratory bath tub may be designed to produce vibratory patterns within the reservoir of the tub that make it difficult for a user to easily discern the positions from which the vibrations are originating (i.e., the positions of the transducers). One way to produce such a vibration pattern is to use a substantial number of transducers (e.g., eight transducers) distributed across different positions on the reservoir so that the vibratory stimuli originate from many different positions. In a bath tub having a rectangular reservoir, for example, two transducers may be mounted on each of the four sides of the reservoir. Using a large number of transducers to effect the vibratory stimulus can substantially increase the cost of the vibroacoustic bathing system.

In some exemplary embodiments, vibroacoustic bathing systems are provided that achieve a substantially similar vibratory stimulus to a user when submerged within water in the reservoir using fewer transducers than previous systems. Some embodiments use only four transducers mounted at particular locations around the reservoir to provide the vibratory stimulus. The four transducers may be distributed around the reservoir in a manner such that, when a wall of the reservoir is partitioned into four sections, only a single transducer is mounted against each section of the wall and no other transducers are mounted against the wall. The four transducers may be offset from axes of the reservoir such that, when the vibratory stimuli produced by the individual transducers are combined in the water, a surrounding vibration effect may be felt by the user that may feel as if the vibrations are originating from all around the user rather than from four distinct locations. Using only four transducers positioned at particular locations may help to reduce interference between vibratory waves produced by individual transducers that often occurs in systems using a greater number of transducers.

According to some embodiments, a touch sensitive user interface device is provided that is configured for operation in wet environments such as for use in controlling features of a bath or shower. The user interface device may include a resistive touchscreen device configured to provide display images to a user and to receive user selections by sensing when particular portions of the resistive touchscreen are pressed. The user interface device may be configured to allow a user to control features relating to aural and/or vibratory stimuli being generated using transducers associated with the bath or shower. For example, the user interface device may be used to change a song or theme that is being played and/or to change the volume or intensity of all or a subset of the transducers. In some embodiments, the user interface device may be configured to allow a user to control colors of lights positioned on or near the bath or shower fixture.

The user interface device may be designed to be resistant to moisture and/or cleaning chemicals that can damage the resistive touchscreen device. For example, the user interface device may include a protective screen (e.g., a mylar screen) and a housing, and the protective screen may be sealed to a front cover of the housing to prevent the ingress of moisture through a front portion of the user interface device. A potting material or a gasket may be positioned between the housing and the resistive touchscreen device near a joint between the front and back covers of the housing and may prevent moisture from entering the device at the joint and coming into contact with the resistive touchscreen device. In some embodiments, some components of the user interface device (e.g., the protective screen and/or housing) may include a coating or additive material to help prevent against damage from cleaning chemicals that may be used to clean the bath or shower.

Figure 2:
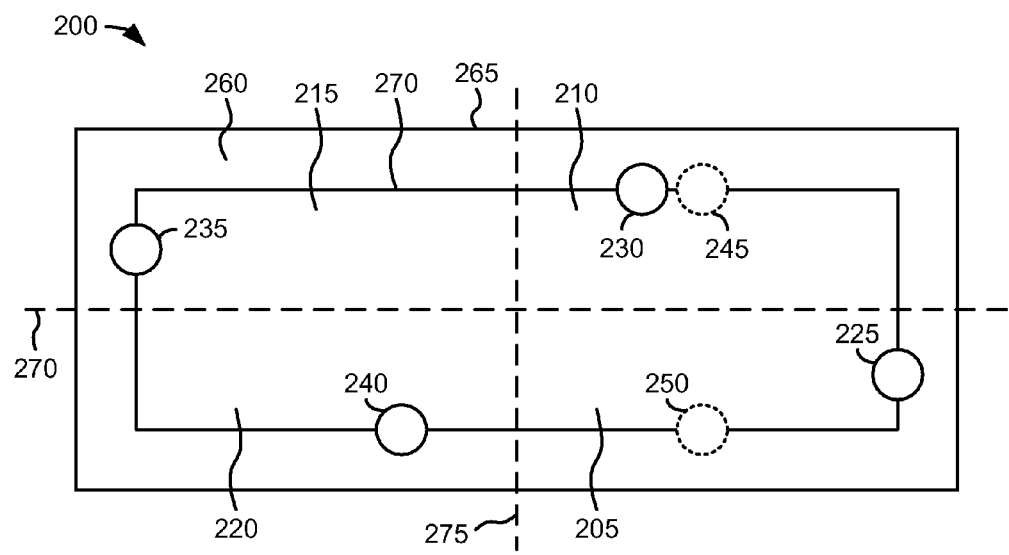
FIG. 2 is a simplified plan view of another bath tub illustrating a position of a plurality of transducers according to an exemplary embodiment.

Referring now generally to FIGS. 1 and 2, plan views of two vibroacoustic bath tubs having different transducer configurations are shown according to exemplary embodiments. The vibroacoustic bath tubs include multiple transducers mounted in an energy transmitting relation with a reservoir of the bath tubs, such as mounted against a side wall of the bath tubs. Some of the transducers are vibratory transducers that are mounted below a water line (e.g., a maximum water level) of the bath tubs and configured to generate vibratory stimuli within water in the bath tubs by vibrating the reservoir. Some of the transducers are audio transducers that are mounted above the water line and are configured to generate aural stimuli (e.g., play music or other sounds). Both the audio transducers and the vibratory transducers may operate by causing the reservoir to vibrate at particular frequencies. In some embodiments, the transducers may all include one type of transducer, with the primary difference being the mounting position of the transducers (e.g., above or below the water line). In some embodiments, the vibratory transducers and audio transducers may be different types of transducers.

In some embodiments, the vibratory transducers may be arranged and/or controlled to create a perceived spatial "center" around a certain point in the reservoir, such that the user perceives that the vibratory sensation is originating from all around the user (e.g., creating a "surround vibration" sensation) rather than from discrete points at which the vibratory transducers are located. The location of the transducers and input signals used to drive the transducers may be designed to create a spatial center near a centroid of the reservoir or the spatial center may be focused in another region of the reservoir, such as nearer to a point where a user's head or feet would be positioned during use. In some embodiments, the input signals may be used to change the position of the spatial center. For example, the input signals may be used to create a desired vibration pattern that moves the spatial center from one position to another, such as from near the user's head to near the user's legs and feet. In some embodiments, a separate spatial center may exist for the vibratory transducers and the audio transducers, such that the perception of the user is that the vibratory stimuli are centered around a different position than the aural stimuli. In some embodiments, the spatial centers for the vibratory and aural stimuli may be approximately the same lateral position (i.e., a same approximate position when the reservoir is viewed from an overhead plan view).

One way of producing the desired "surround" sensation in which it is difficult for a user to discern discrete origination points of vibration is to use a relatively large number of transducers distributed around the bath tub reservoir. FIG. 1 is a basic overhead plan view of a vibratory bath tub 100 that uses eight vibratory transducers 105 to produce vibratory sensations according to an exemplary embodiment. The transducers configuration illustrated in FIG. 1 is similar to that illustrated in co-pending U.S. patent application Ser. No. 12/408,777, published as U.S. Patent Application Publication No. 2009/0241254, which is assigned to the assignee of the present application. In addition to the eight vibratory transducers 105, bath tub 100 also includes two audio transducers 110 that are positioned above the water line of bath tub 100 and are configured to generate aural stimuli. A control system for bath tub 100 may be configured to drive audio transducers 110 and vibratory transducers 105 using different input files (e.g., an audio track and a vibration track).

Bath tub 100 uses eight vibratory transducers 105 distributed in a pattern around bath tub 100 to achieve the desired vibratory stimuli when water is inserted into bath tub 100. Vibratory transducers 105 are positioned such that two vibratory transducers 105 are proximate to a head end of bath tub 100, two vibratory transducers 105 are proximate to a foot end of bath tub 100, two vibratory transducers 105 are positioned on a first side of bath tub 100 (one nearest the head end and one nearest the foot end), and two vibratory transducers 105 are positioned on a second side of bath tub 100 (again, one nearest the head end and one nearest the foot end). The illustrated vibratory transducer configuration is symmetrical across both the major axis 115 and the minor axis 120 of the elliptically-shaped bath tub 100. For example, a vibratory transducer 105 positioned at a head end of bath tub 100 has a corresponding vibratory transducer 105 positioned in a same position across minor axis 120 at a foot end of bath tub 100 and another corresponding transducer 105 also positioned at a head end of bath tub 100 across major axis 115. When split into four quadrants based on the intersection of major axis 115 and minor axis 120 as illustrated in FIG. 1, each quadrant includes two vibratory transducers 105. While a larger number of vibratory transducers, such as the eight transducer configuration of bath tub 100, can help ensure that the desired "surround" sensation can be achieved, it also substantially increases the cost of vibroacoustic bath tub 100. In addition to the cost of the transducers themselves, adding more transducers may require other additional components such as additional transducer mounting assemblies, additional amplifiers to drive the transducers, and/or additional processors to process the signals used to drive the transducers.

The inventors have discovered that a similar user experience may be achieved using only four vibratory transducers by placing the vibratory transducers at particular positions relative to one another in the bath tub reservoir. FIG. 2 is a basic overhead plan view of a vibratory bath tub 200 that uses only four vibratory transducers 225, 230, 235, 240 to produce similar vibratory wave patterns to those produced in the configuration used in bath tub 100. Bath tub 200 includes four vibratory transducers 225, 230, 235, 240 distributed around a reservoir 260 of bath tub 200. Vibratory transducers 225, 230, 235, 240 are mounted in energy transmitting relation with (e.g., mounted against a side of) reservoir 260 and are configured to vibrate reservoir 260 at particular frequencies to effect desired vibratory patterns in water inserted into reservoir 260. Bath tub 200 also includes two audio transducers 245, 250 configured to vibrate reservoir 260 to emit an aural stimulus (e.g., play music or other sounds, such as soothing nature sounds). Vibratory transducers 225, 230, 235, 240 and audio transducers 245, 250 may be controlled through input signals received from a control circuit. The control circuit may be configured to generate signals configured to coordinate the operation of vibratory transducers 225, 230, 235, 240 and audio transducers 245, 250 so that the aural sensations and vibratory sensations experienced by the user are coordinated (e.g., the vibratory stimuli are coordinated with music being played using audio transducers 245, 250).

Vibratory transducers 225, 230, 235, 240 of bath tub 200 are distributed in a particular pattern around reservoir 260 to increase the effect each vibratory transducer has on the vibratory stimuli experienced by the user. In the illustrated exemplary embodiment of FIG. 2, bath tub 200 has a rectangular shape having a wall that includes two end walls and two side walls. Only a single vibratory transducer is mounted against each of the end walls and side walls. The wall of reservoir 260 may be partitioned into four equal sections 205, 210, 215, 220 based on the intersection of its axes of symmetry, lengthwise axis 270 and widthwise axis 275. Each of sections 205, 210, 215, 220 includes only a single vibratory transducer 225, 230, 235, 240. Neither lengthwise axis 270 nor widthwise axis 275 intersect the position of vibratory transducers 225, 230, 235, 240, and the position of vibratory transducers 225, 230, 235, 240 is not symmetrical across either of the axes of symmetry 270, 275 of bath tub 200. In some embodiments, vibratory transducers 225 and 235 (mounted against the ends of reservoir 260) may be offset by a same first lateral distance from lengthwise axis 270 and vibratory transducers 230 and 240 (mounted against the sides of reservoir 260) may be offset by a same second lateral distance from widthwise axis 275. In such embodiments, if the vertices represented by vibratory transducers 225, 230, 235, 240 were connected to one another, a parallelogram shape would result. In some embodiments, the lateral distance from vibratory transducers 225 and 235 to lengthwise axis 270 may be smaller than the lateral distance from vibratory transducers 230 and 240 to widthwise axis 275.

In some embodiments, bath tub 200 may have a shape other than a rectangular shape. For example, in some embodiments, bath tub 200 may have an ovular shape, such as an elliptical shape similar to the shape of bath tub 100. Such a bath tub may have an elliptical reservoir that is symmetrical across a major axis (i.e., an axis that travels across a maximum length of the reservoir) and a minor axis (i.e., an axis that travels across a maximum width of the reservoir). The elliptical reservoir may be partitioned into four equal sections based on the intersection of the major and minor axes with the reservoir. The four vibratory transducers may be positioned such that only a single vibratory transducer is mounted against each of the four sections. In some embodiments, the vibratory transducers may be positioned such that two transducers are positioned diagonally from one another across the reservoir and are offset from the major axis by a same first lateral distance (e.g., distance from the axis when traveling across the curvature of the reservoir wall). The other two transducers may be positioned diagonally from one another across the reservoir and may be offset from the minor axis by a same second lateral distance. The position of the transducers may be asymmetrical across both the major axis and the minor axis. In some embodiments, the bath tub may include other types of shapes, such as a non-elliptical ovular shape (e.g., an "egg" shape) or a non-uniform shape. In such embodiments, the vibratory transducers may be positioned such that, when the bath tub reservoir is partitioned into four sections, only a single vibratory transducer is mounted against a particular section.

The relative positional relationship of the four vibratory transducers 225, 230, 235, 240 enables bath tub 200 to achieve a similar vibratory sensation for the user with approximately the same energy input as in the vibratory transducer configuration of bath tub 100 illustrated in FIG. 1 that utilizes eight vibratory transducers, or twice as many vibratory transducers as bath tub 200. One reason for the increased efficiency is that the positioning of the four vibratory transducers 225, 230, 235, 240 in bath tub 200 reduces the interference between vibratory waves of the individual vibratory transducers. In the eight-transducer configuration of bath tub 100, the inventors have determined that, in some instances, vibratory waves produced by some transducers may interfere with vibratory waves produced by other transducers. While it may intuitively seem that a greater number of transducers would be able to produce a greater vibratory stimulation, the large number of transducers in bath tub 100 may actually generate vibratory waves that partially cancel one another, reducing the vibratory stimulation experienced by the user. Vibratory transducers 225, 230, 235, 240 in bath tub 200 are positioned in a relative arrangement (e.g., an asymmetric configuration) that reduces the interference and cancelling effect between vibratory waves of the individual vibratory transducers. Bath tub 200 may also be able to produce a similar vibratory stimulation as bath tub 100 at a lesser cost, as fewer vibratory transducers are required as well as various components used to mount and/or drive the transducers such as additional transducer mounting assemblies, additional amplifiers to drive the transducers, and/or additional processors to process the signals used to drive the transducers.

Figure 3:
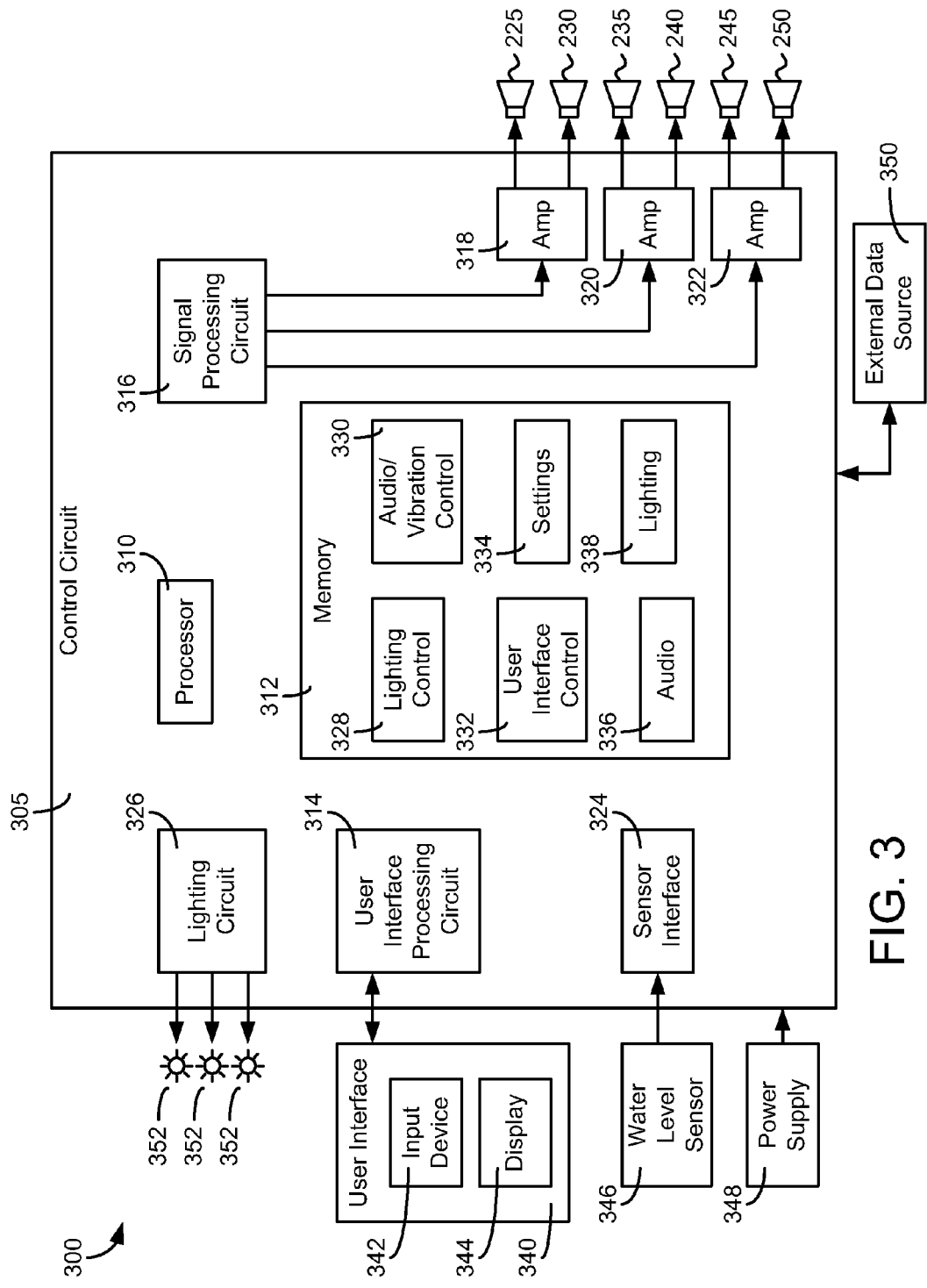
FIG. 3 is a block diagram of a user experience system for a vibroacoustic bath according to an exemplary embodiment.

Referring now to FIG. 3, a block diagram of a user experience system 300 for a vibroacoustic bathroom fixture is shown according to an exemplary embodiment. In some embodiments, user experience system 300 may be used to control the vibratory and aural stimuli produced by transducers in a vibroacoustic bath tub (e.g., bath tub 200).

User experience system 300 includes a control circuit 305 configured to control the operation of the various features of the user experience system 300. Control circuit 305 includes a processor 310 and a memory 312. Processor 310 may include any general purpose or special purpose processor (e.g., FPGA, CPLD, ASIC, RISC, etc.). Memory 312 may include any type of computer or machine-readable medium (e.g., RAM, ROM, solid state memory, flash memory, hard disk, removable storage media, optical discs, etc.). Control circuit 305 may be configured to receive operating power from a power supply 348. Power supply 348 may be an alternating current (AC) switching power supply that is configured to receive input power from a standard wall outlet (e.g., 120 VAC) and to rectify the input power and output direct current (DC) power for use by control circuit 305.

Memory 312 may include modules used to implement different features of user experience system 300. The modules may be implemented as computer or machine-readable instructions or program code that, when executed by processor 310, cause processor 310 to perform functions associated with the modules. For example, an audio and vibration control module 330 is configured to control audio and vibratory transducers of the vibroacoustic fixture (e.g., bath tub) to produce desired aural and vibratory stimuli for a user. Audio and vibration control module 330 may be configured to select an audio file for use in producing the aural and vibratory stimuli from an audio database 336 that includes a plurality of different audio files. The audio files may represent music or other types of sounds, such as soothing nature sounds. In some embodiments, the audio files may be selected from an external data source 350 (e.g., USB flash drive, Secure Digital (SD) card, miniSD, CompactFlash, removable optical media, etc.). For example, a USB flash drive may be entered into an input port of user experience system 300 (e.g., a Universal Serial Bus port), and audio and vibration control module 330 may be configured to extract audio files from the USB flash drive. This may provide an easy way for new audio files to be added to user experience system 300 for use in producing the aural and vibratory stimuli.

Audio and vibration control module 330 (e.g., in conjunction with processor 310 and/or other hardware circuits) may be configured to convert the audio files from a file format (e.g., MP3) into a streaming audio signal including multiple channels. The audio signal may be provided to a signal processing circuit 316 configured to condition the audio signal, for example by adjusting the frequency and/or amplitude of components (e.g., channels) of the signal, and transmit various components of a conditioned output signal to a plurality of amplifiers 318, 320, 322. Signal processing circuit 316 may transmit a first vibratory portion (e.g., corresponding to a first vibratory channel) of the signal to amplifier 318, which amplifies the input signal and outputs signals to drive vibratory transducers 225 and 230 to produce desired vibratory patterns. Signal processing circuit 316 may transmit a second vibratory portion (e.g., corresponding to a second vibratory channel) of the signal to amplifier 320, which amplifies the input signal and outputs amplified signals to drive vibratory transducers 235 and 240 to produce desired vibratory patterns. Signal processing circuit 316 may transmit one or more audio portions (e.g., audio channels) of the signal to amplifier 322, which amplifies the input signal and outputs amplified signals to drive audio transducers 245 and 250 to produce desired aural patterns. In some embodiments, user experience system 300 may be able to provide the desired aural and vibratory stimuli using less processing electronics than a user experience system using a greater number of vibratory transducers (e.g., eight). For example, user experience system 300 may utilize only a single main microprocessor and/or single signal processing circuit, where a user experience system with eight vibratory transducers may require multiple microprocessors and/or signal processing circuits.

A lighting control module 328 may be configured to control one or more lights 352 located on or near the vibroacoustic fixture. Lights 352 may be configured to emit light having a plurality of different colors, such as blue, pink, red, green, orange, and/or other colors. For example, lights 352 may include a plurality of selectable color filters configured to determine a color of light emitted from lighting units including lights 352 or may include multi-colored lights (e.g., light emitting diodes, filament bulbs, fiber optic strands, etc.) that are selectively activated and deactivated to emit desired light colors. Lights 352 may be used as chromatherapy devices that provide visual stimuli to a user of the vibroacoustic fixture designed to further relax the user in conjunction with the aural and vibratory stimuli provided using the audio and vibratory transducers. Lighting control module 328 may be configured to select a lighting color to be emitted by lights 352 from among the available lighting colors that lights 352 are capable of emitting. The selected lighting color may be provided to a lighting circuit 326 that is configured to transmit signals to lights 352 configured to cause the lights 352 to emit the selected light color. In some embodiments, available lighting options and/or active lighting settings may be stored in a lighting database 338 within memory 312 and/or may be accessed from external data source 350.

In some embodiments, lighting control module 328 may be configured to control lights 352 based on different user-selectable modes. In a first mode, lighting control module 328 may cause lights 352 to emit light of a single user-selected color. For example, a user may select the first mode and a color to be emitted, such as blue, and lighting control module 328 may be configured to cause lights 352 to emit blue light until a different color or different mode is selected by the user. In a second mode, lighting control module 328 may cause lights 352 to cycle through different colors. In one embodiment of the second mode, lighting control module 328 may continuously cycle through all of the available colors until a different mode is selected (e.g., at regular predetermined intervals). In some embodiments, lighting control module 328 may be configured to coordinate the visual stimuli provided by lights 352 with the aural and vibratory stimuli coordinated by audio and vibration control module 330.

A user interface control module 332 may be configured to receive input from a user of the vibroacoustic fixture and to set various options and settings used by lighting control module 328 and/or audio and vibration control module 330 to provide aural, vibratory, and visual stimuli to a user. User interface control module 332 may be configured to receive user input from a user interface device 340 through a user interface processing circuit 314 of control circuit 305. User interface device 340 may include an input device 342 configured to be manipulable by the user to provide the user input. In some embodiments, user interface device 340 may include a display 344 or other indicator device configured to indicate to a user which options are currently selected. In some embodiments, user interface device may include a touchscreen display device (e.g., a resistive touchscreen display) configured to provide display images to a user and to receive input from the user in the manner of user presses on portions of the display representing different options or selections. User interface control module 332 may be configured to store selected options in a settings database 334 of memory 312.

User interface control module 332 may be configured to receive music or relaxation theme user selections that may be used to determine audio files used to provide the aural and vibratory stimuli. Different music or theme options may be displayed to the user on display 344 as different icons. When the user selects one of the icons using input device 342, a signal representing the selection may be received at user interface processing circuit 314. User interface control module 332 may be configured to change the currently selected audio file to the audio file represented by the user selection. Audio and vibration control module 330 may then be configured to use the newly selected audio file as the underlying file for producing the aural and vibratory stimuli.

User interface control module 332 may be configured to receive lighting (e.g., chromatherapy) selections from a user that may be used to determine the color to be emitted by lights 352. One or more lighting selection display images may be presented to the user on display 344. In one exemplary mode, the user may select a desired color using input device 342 and a signal representing the selected color and/or mode may be received at user interface processing circuit 314. User interface control module 332 may be configured to change the currently selected lighting mode and color to the selected mode and color. Lighting control module 328 may then be configured to cause lights 352 to emit light of the selected color. In some embodiments, user interface control module 332 may allow the user to select a second exemplary mode and, upon detecting the user selection, may direct lighting control circuit 328 to implement the second mode in which the color of lights 352 is continuously cycled between the available colors of lights 352.

In some embodiments, user interface control module 332 may be configured to control other settings of user experience system 300. For example, user interface control module 332 may allow the user to place user experience system into an auxiliary audio input mode in which the audio signal used to produce the aural and vibratory stimuli is received from an external media device (e.g., connected via an auxiliary audio input port, such as a mini jack audio input). In some embodiments, user interface control module 332 may allow the user to change a language used in the display images presented to the user. In some embodiments, user interface control module 332 may allow the user to change the brightness or contrast of display 344. In some embodiments, user interface control module 332 may allow the user to change the intensity of the audio and/or vibratory transducers and/or lights 352.

In some embodiments, control circuit 305 may include a sensor interface 324 configured to receive input from one or more sensors located on or near the vibroacoustic fixture. For example, sensor interface 324 may receive input from a water level sensor 346 configured to sense a level of water (e.g., sense whether the water is above a particular level) in a reservoir of a vibroacoustic bath tub. Audio and vibration control 330 may be configured to determine whether the water level is above a predetermined level (e.g., above a level at which the vibratory transducers are mounted) before activating the vibratory transducers.

Referring now generally to FIGS. 4A through 4H, various views of an example user interface device 400 that may be used in conjunction with a bathroom fixture such as a bath or shower are shown according to an exemplary embodiment. User interface device 400 may be used to provide display images to a user of the bathroom fixture and to receive touch input from the user for use in configuring features of a user experience system of the bathroom fixture. In some embodiments, user interface 400 may be used to receive user input relating to features of a user experience system for a vibroacoustic fixture such as user experience system 300 illustrated in FIG. 3.

Figure 4A:
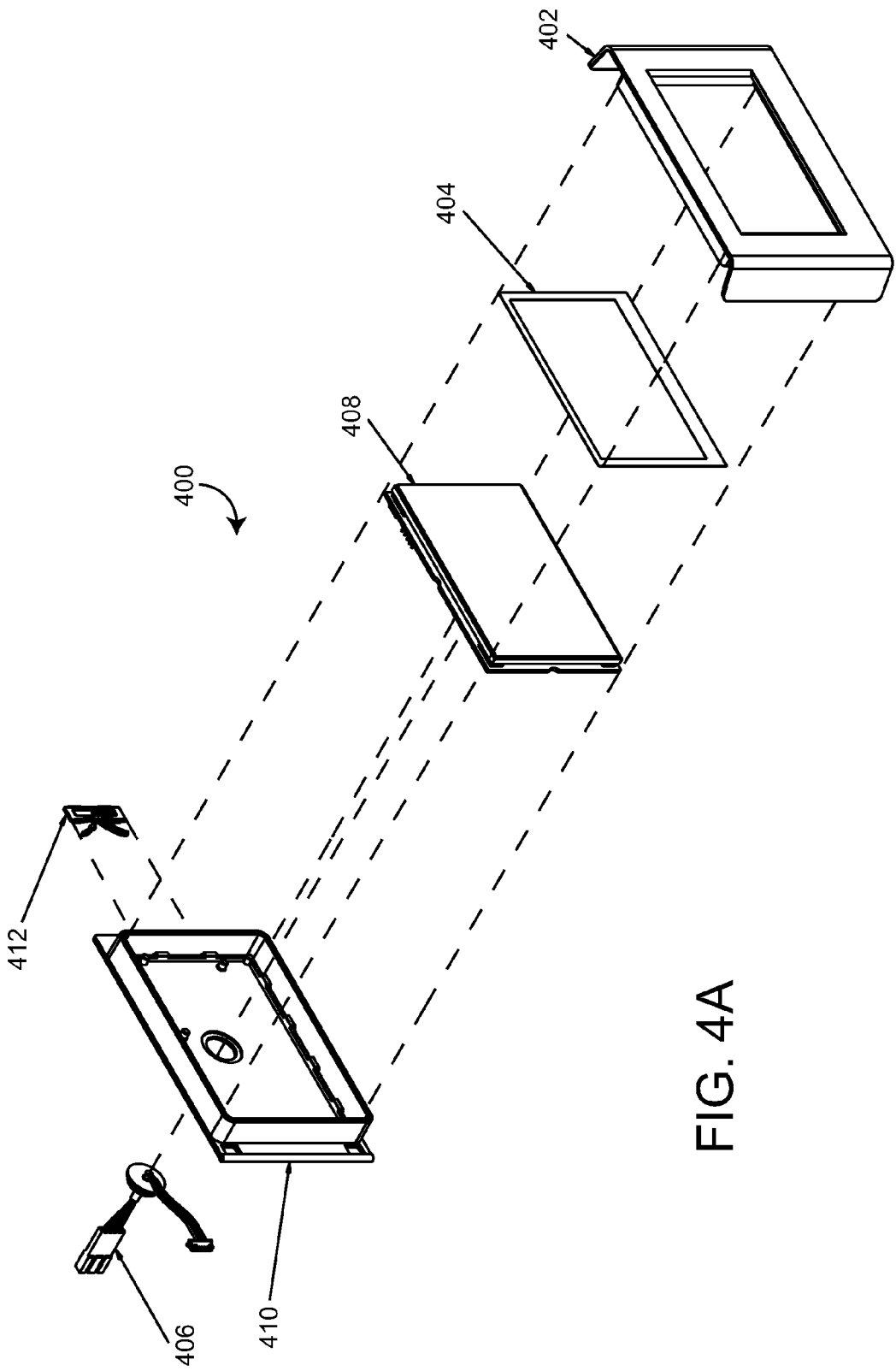
FIG. 4A is an exploded view of various components of a user interface device according to an exemplary embodiment.

FIG. 4A illustrates an exploded view of user interface device 400. User interface device 400 includes a touchscreen display device 408 configured to provide display images to a user and to receive touch input from the user. The touch input may represent a user touching a particular portion of the display to select an option represented by the corresponding portion of the display image. In some implementations, touchscreen display device 408 may be a resistive touchscreen device that includes multiple conductive layers that are separated by thin spaces. When a user touches a particular point on the display, the layers compress and touch one another and complete electrical circuits. The resistive touchscreen device can determine the location of the touch input based on the location at which the layers are touching. In some embodiments, touchscreen display device 408 may be a capacitive touchscreen device that determines a point at which a user has touched the screen based on a change in electrical properties (e.g., a change in capacitance) resulting from the user's finger touching an electrically conductive coating on the screen. Resistive touchscreen devices may more consistently and accurately detect touch input in wet applications such as bath tub and/or shower applications.

The display portion of touchscreen display device 408 is covered by a protective screen 404 configured to protect touchscreen display device 408 from moisture, chemicals, scratching, and/or other types of hazards. In some embodiments, protective screen 404 may be constructed from a mylar material. A periphery of protective screen 404 may be coated with an adhesive material configured to seal protective screen 404 to a front cover 402 of a housing for user interface device 400. In some embodiments, the adhesive material may include an acrylic adhesive. In some embodiments, protective screen 404 may include a polyester material with a hardcoat laminate designed to protect protective screen 404 and touchscreen display device 408 from damage due to scratching and/or chemicals in bathroom cleaning solutions.

A housing of user interface device 400 may include a front cover 402 that is intended to face towards a user during use and a back cover 410 that is intended to face away from the user. Front cover 402 and back cover 410 may be welded to one another to provide rigidity to user interface device 400 and to help protect against the ingress of moisture. In some embodiments, front cover 402 and/or back cover 410 may be coated with a protective coating material, such as an ultraviolet inhibiting material, to provide resistance against damage from chemicals that may be used in bathroom cleaning solutions. A connector cable 406 may be connected to touchscreen display device 408 on one end and to a control circuit associated with the bath or shower on the other end and used to transmit and receive signals between user interface device 400 and the control circuit. A mounting fastener 412 (e.g., a spring clip) may be used to secure user interface device 400 to a mounting structure on or near the bath or shower.

Figure 4B:
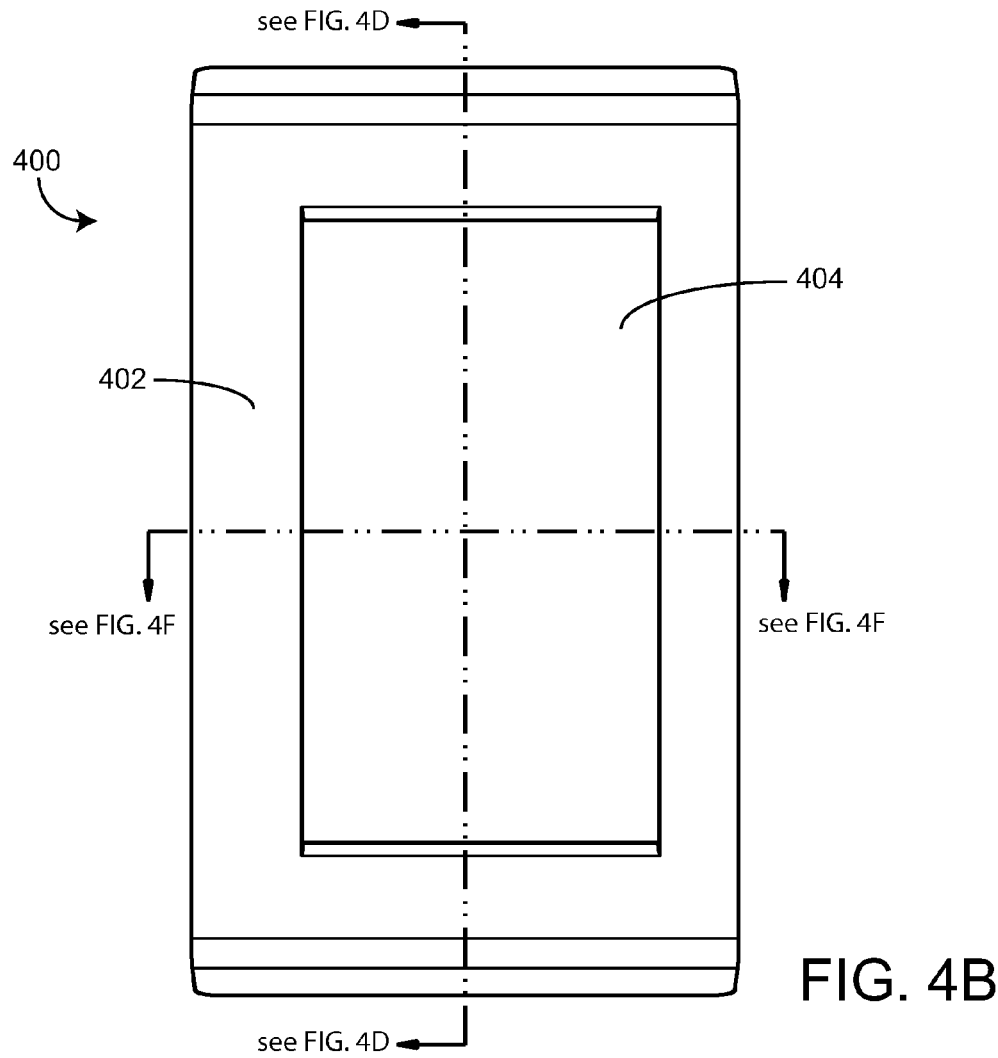
FIG. 4B is a schematic illustration of a front view for the user interface device shown in FIG. 4A according to an exemplary embodiment.

FIG. 4B illustrates a front view of user interface device 400, including front cover 402 and protective screen 404. The interface between front cover 402 and protective screen 404 may be sealed by an adhesive material to prevent the ingress of moisture in wet environments that may damage touchscreen display device 408.

Figure 4C:
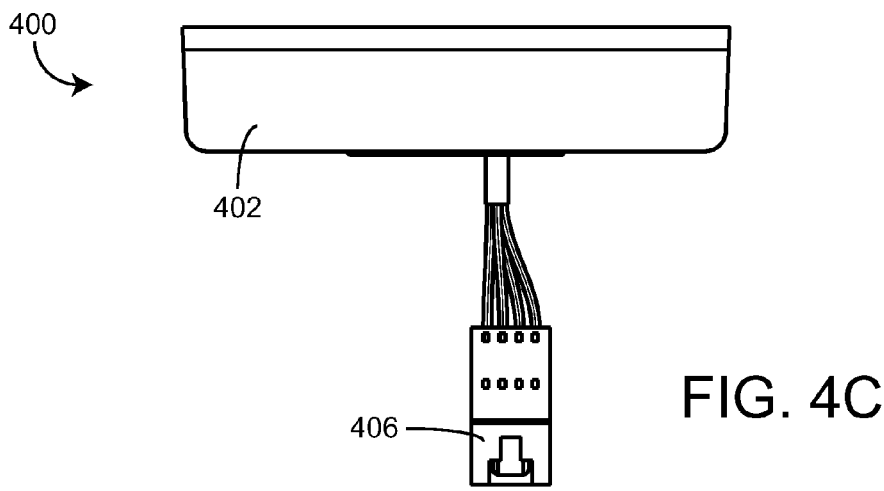
FIG. 4C is a schematic illustration of a side view for the user interface device shown in FIG. 4B according to an exemplary embodiment.

FIG. 4C illustrates a side view of user interface device 400. After assembly, a portion of connector cable 406 extends out of a back of the device and may be connected with a corresponding connector on a mounting system to which user interface device 400 may be mounted. The corresponding connector may be electrically coupled to a control system for the bath or shower. A portion of connector cable 406 is contained within the housing and electrically connected to touchscreen display device 408.

Figure 4D:
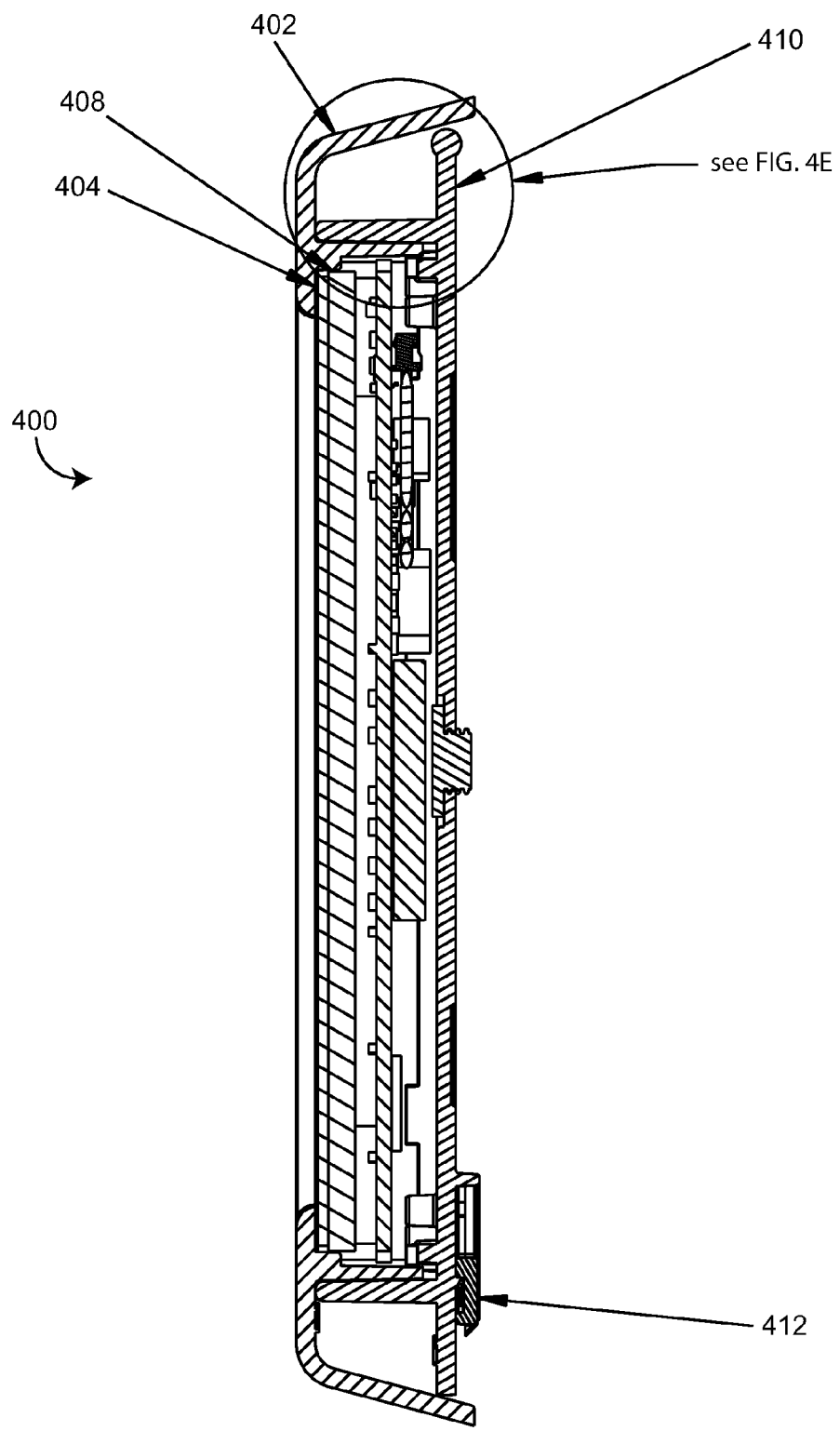
FIG. 4D is a schematic illustration of a lengthwise cross-sectional view for the user interface device shown in FIG. 4B according to an exemplary embodiment.

FIG. 4D illustrates a lengthwise cross-sectional view of user interface device 400. FIG. 4D illustrates the internal layering of the components of user interface device 400. Front cover 402 and protective screen 404 may be sealingly coupled to one another by an adhesive material. Behind protective screen 404 is touchscreen display device 408, including various electronic components mounted on a circuit board that are configured to drive the display of touchscreen display device 408 and to detect touch input from a user on the display. Behind touchscreen display device 408 is back cover 410, and back cover 410 is welded to front cover 402 (e.g., via ultrasonic welding) to form a rigid user interface structure.

Figure 4E:
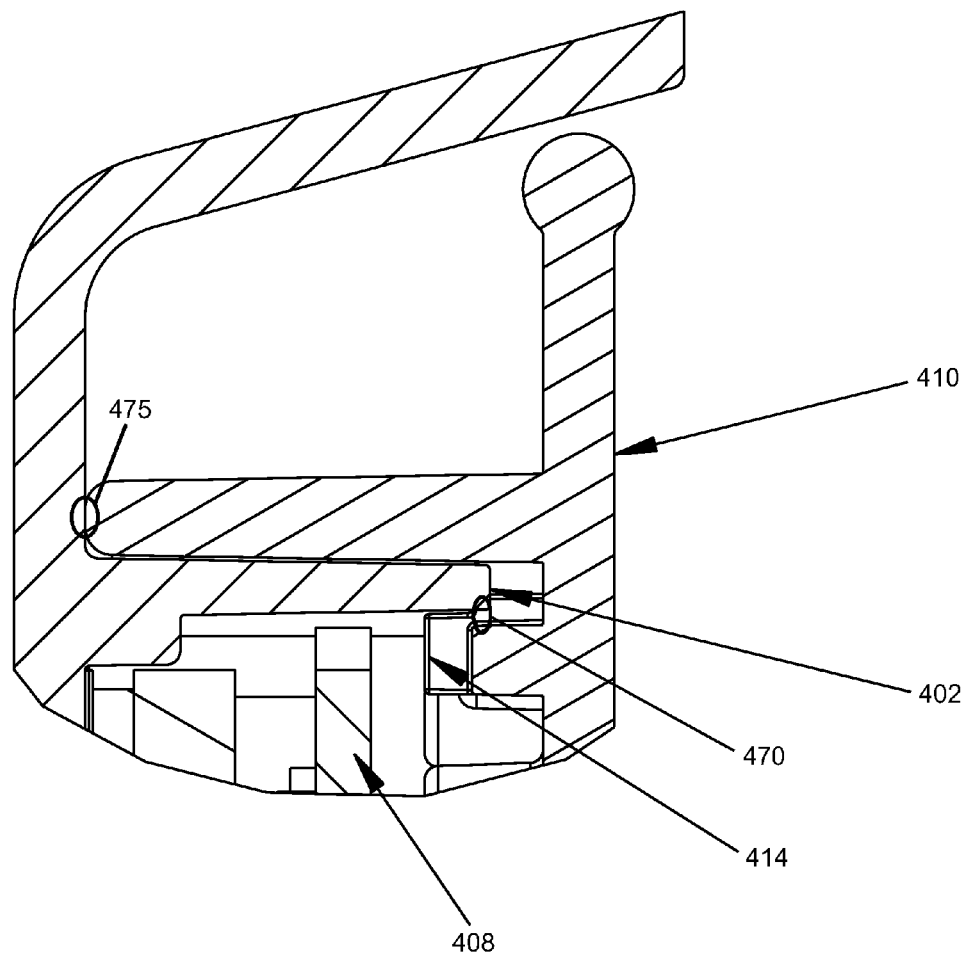
FIG. 4E is a detailed view for an end of the cross-sectional view shown in FIG. 4D for the user interface device according to an exemplary embodiment.

FIG. 4E illustrates a close-up view of a side of the cross-sectional view for user interface device 400 as shown in FIG. 4D. Potting material (e.g., a silicone elastomer material) may be inserted at a position 414 between touchscreen display device 408, front cover 402, and back cover 410 (e.g., near a joint where front cover 402 and back cover 410 connect). Back cover 410 may include a plurality of protrusions 465 near a back edge of back cover 410 that may be welded to protrusions of front cover 402 at or near a position 470. Front cover 402 and back cover 410 may also be welded together at a position 475 near a face portion of front cover 402. The potting material may seal a back portion of user interface device 400 and prevent against the ingress of moisture at the joint between front cover 402 and back cover 410. In some embodiments, a gasket (e.g., a soft cellular silicone material) may be inserted between touchscreen display device 408 and the housing instead of the potting material to seal the rear portion of user interface device 400.

Figure 4F:
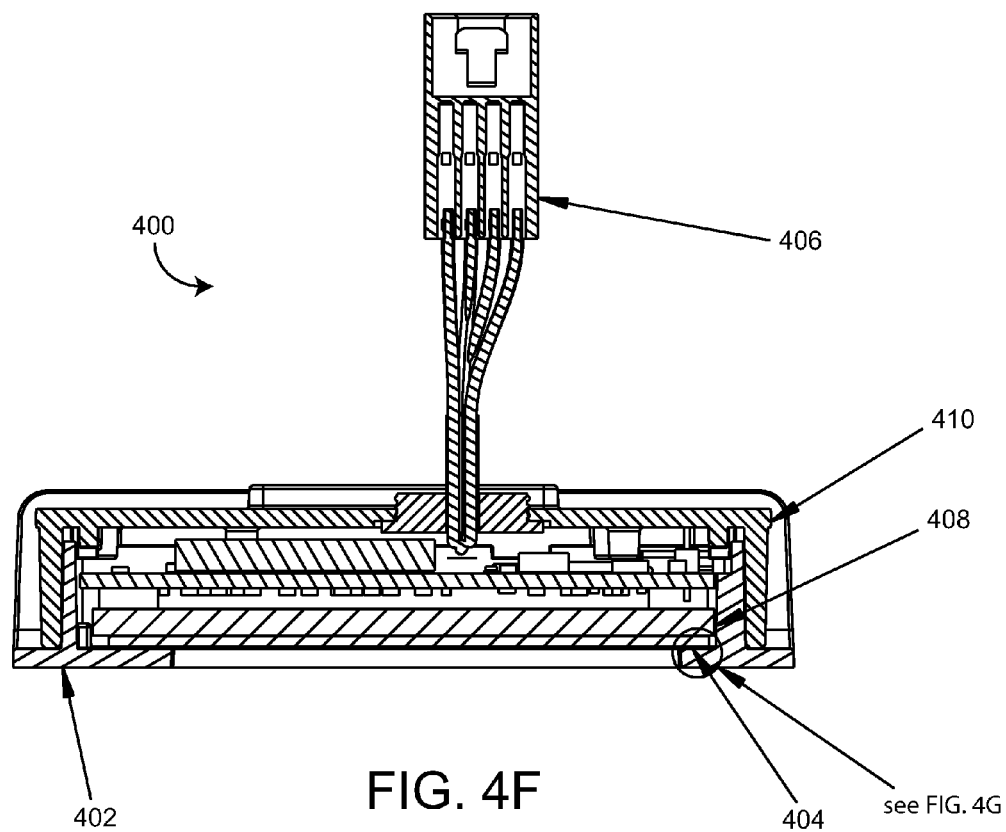
FIG. 4F is a schematic illustration of a widthwise cross-sectional view for the user interface device shown in FIG. 4B according to an exemplary embodiment.
Figure 4G:
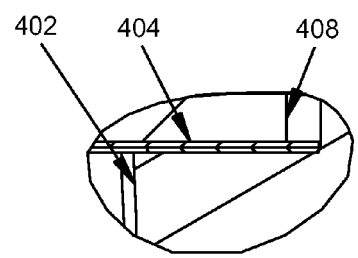
FIG. 4G is a detailed view for a portion of the cross-sectional view shown in FIG. 4F for the user interface device according to an exemplary embodiment.

FIG. 4F illustrates a widthwise cross-sectional view of user interface device 400. As in FIG. 4D, the internal layering of the components of user interface device 400 can be seen in FIG. 4F. FIG. 4G illustrates a close-up view of a front portion of user interface device 400 as shown in FIG. 4F. FIG. 4G illustrates a detailed view of the layering of front cover 402, protective screen 404, and touchscreen display device 408. As illustrated in FIG. 4G, protective screen 404 includes a hard coating material configured to prevent against scratching and chemical damage. An adhesive may be provided at the illustrated interface between front cover 402 and protective screen 404 to seal front cover 402 and protective screen 404 together to prevent against the ingress of moisture through the front interface.

Figure 4H:
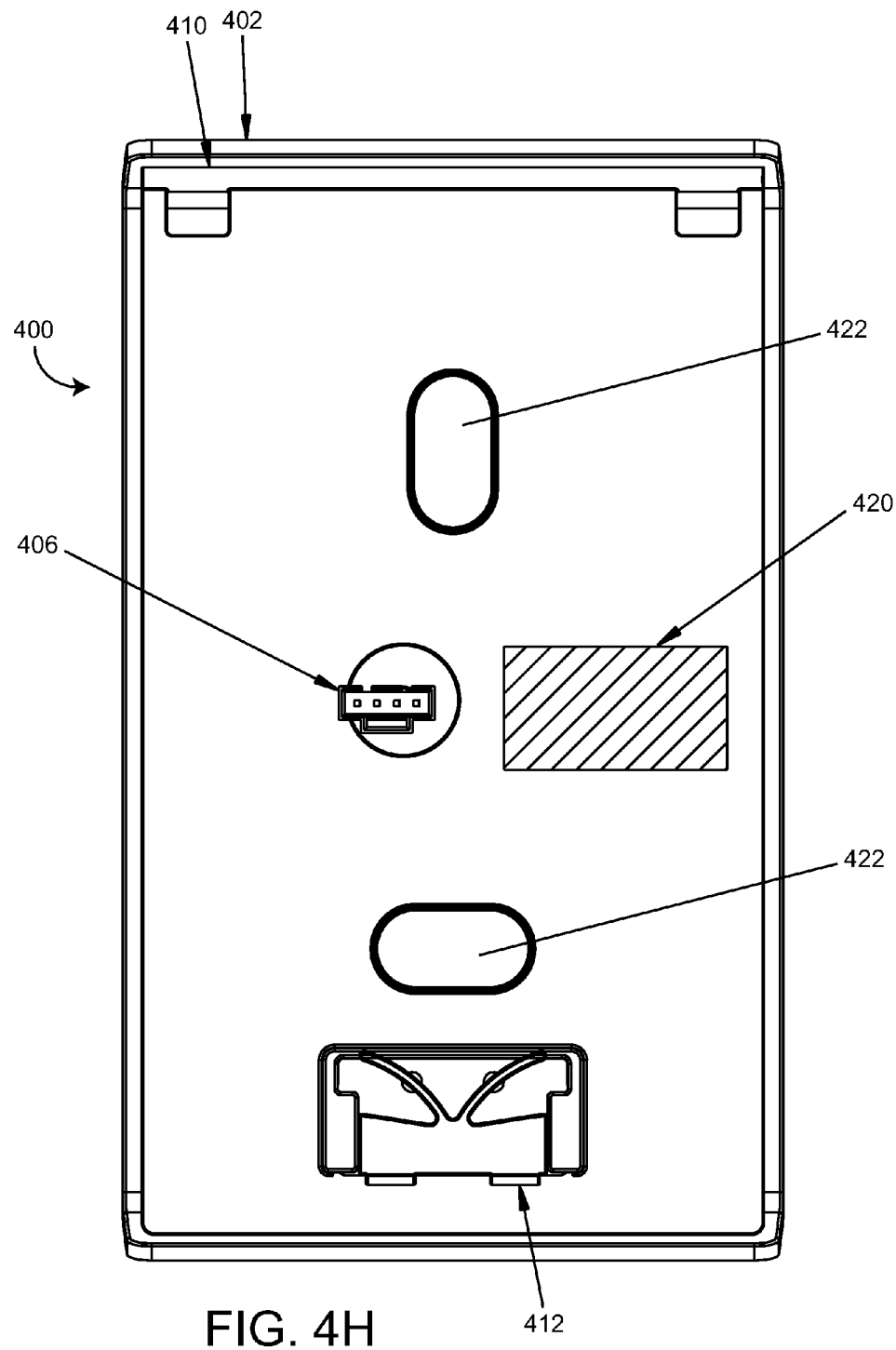
FIG. 4H is a schematic illustration of a rear view for the user interface device shown in FIG. 4B according to an exemplary embodiment.

FIG. 4H illustrates a rear view of user interface device 400. User interface device 400 includes a mounting fastener 412 (e.g., a spring clip) that may be used to easily connect and disconnect user interface device 400 from a mounting system without requiring any portion of user interface device 400 to be disassembled. When user interface device 400 is placed into a mounting system, mounting fastener 412 may compress until fully within place in the mounting system, at which point the tabs of mounting fastener 412 may hold user interface device 400 in place. When the user wishes to remove user interface device 400, a small object may be inserted into a side of user interface device 400 or the mounting system and used to compress mounting fastener 412. Once mounting fastener 412 is compressed, user interface device 400 may be removed from the mounting system. Connector cable 406 extends out of the rear portion of user interface device 400. In some embodiments, a grommet may be included at a hole in back cover 410 through which cable connector 406 extends to provide cable strain relief and to help seal the hole to prevent against moisture ingress. Mounting apertures 420 and 422 may be configured to receive corresponding protrusions from a mounting system upon which user interface device 400 may be mounted.

Figure 5A:
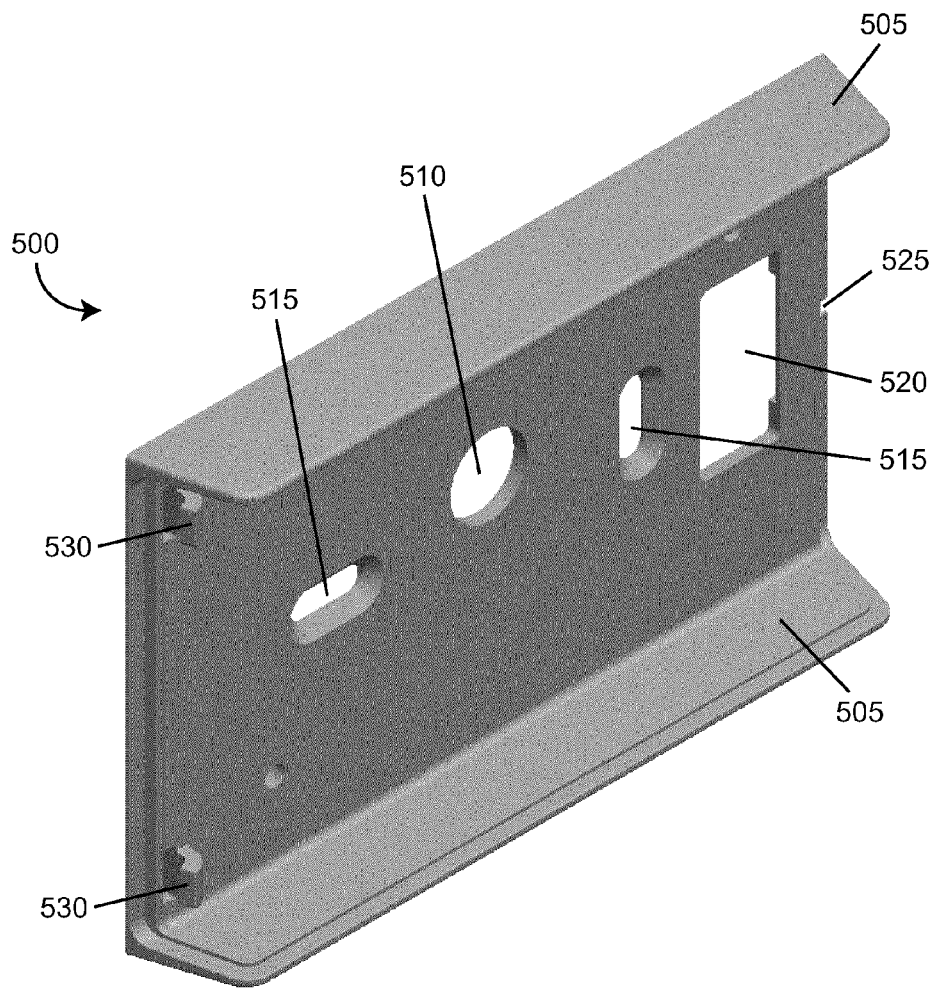
FIG. 5A is a model of a mounting system to which the user interface device shown in FIGS. 4A through 4H may be mounted according to an exemplary embodiment.
Figure 5B:
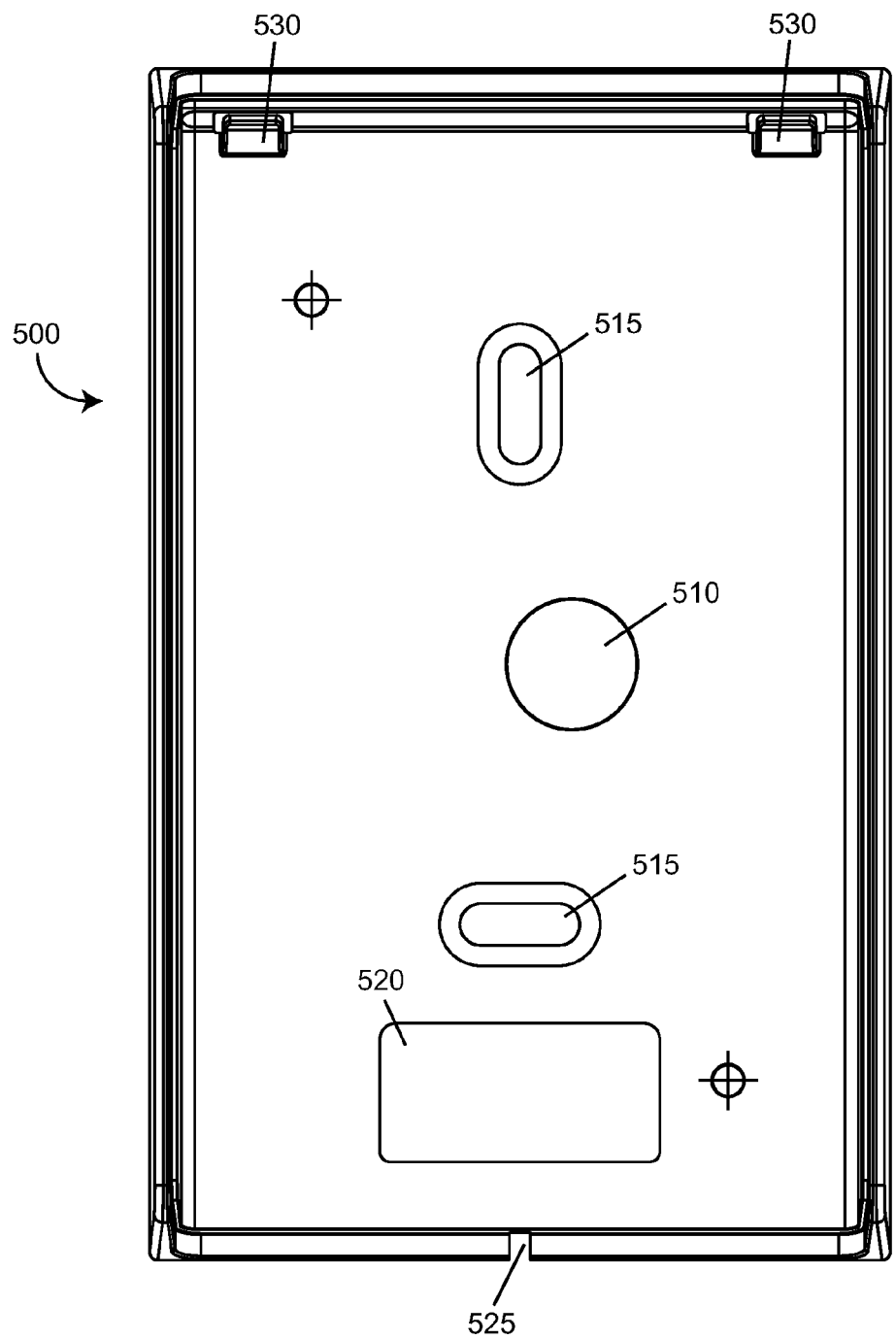
FIG. 5B is a schematic illustration of the mounting system shown in FIG. 5A according to an exemplary embodiment.

Referring now to FIGS. 5A and 5B, a mounting plate 500 to which user interface device 400 may be mounted is shown according to an exemplary embodiment. FIG. 5A is a model of mounting plate 500. Mounting plate 500 includes a top and bottom edges 505 configured to border an upper and lower portion of user interface device 400 when in a mounted configuration. Mounting plate 500 includes a cable aperture 510 through which connector cable 406 may be directed and a mounting fastener aperture 520 into which mounting fastener 412 may be placed when user interface device 400 is mounted in mounting plate 500. In some embodiments, a fastener release slot 525 may be used to release user interface device 400 by placing a small object into fastener release slot 525 and compressing mounting fastener 412. In some embodiments, mounting fastener 412 may be exposed to (and accessible by) a back side of mounting plate 500. Mounting plate 500 includes hooks 530 configured to mate with corresponding slots of user interface device 400 such that, once hooks 530 have mated with the slots, user interface device 400 may be rotated inwards until mounting fastener 412 securely snaps user interface device 400 into place. Mounting apertures 515 of mounting plate 500 may correspond with mounting apertures 420 and 422 of user interface device 400 and may also be configured to receive corresponding protrusions from a mounting system for mounting user interface device 400 in place near the bath tub or shower. FIG. 5B illustrates a schematic line drawing view of a front side of mounting plate 500. The ease of removal of user interface device 400 from mounting plate 500 may help reduce the cost of repair in the event of a problem with user interface device 400 (e.g., a user may be able to remove user interface device 400 and bring it to a repair company rather than requiring a house call from a technician and an in-house repair of user interface device 400).

Figure 6A:
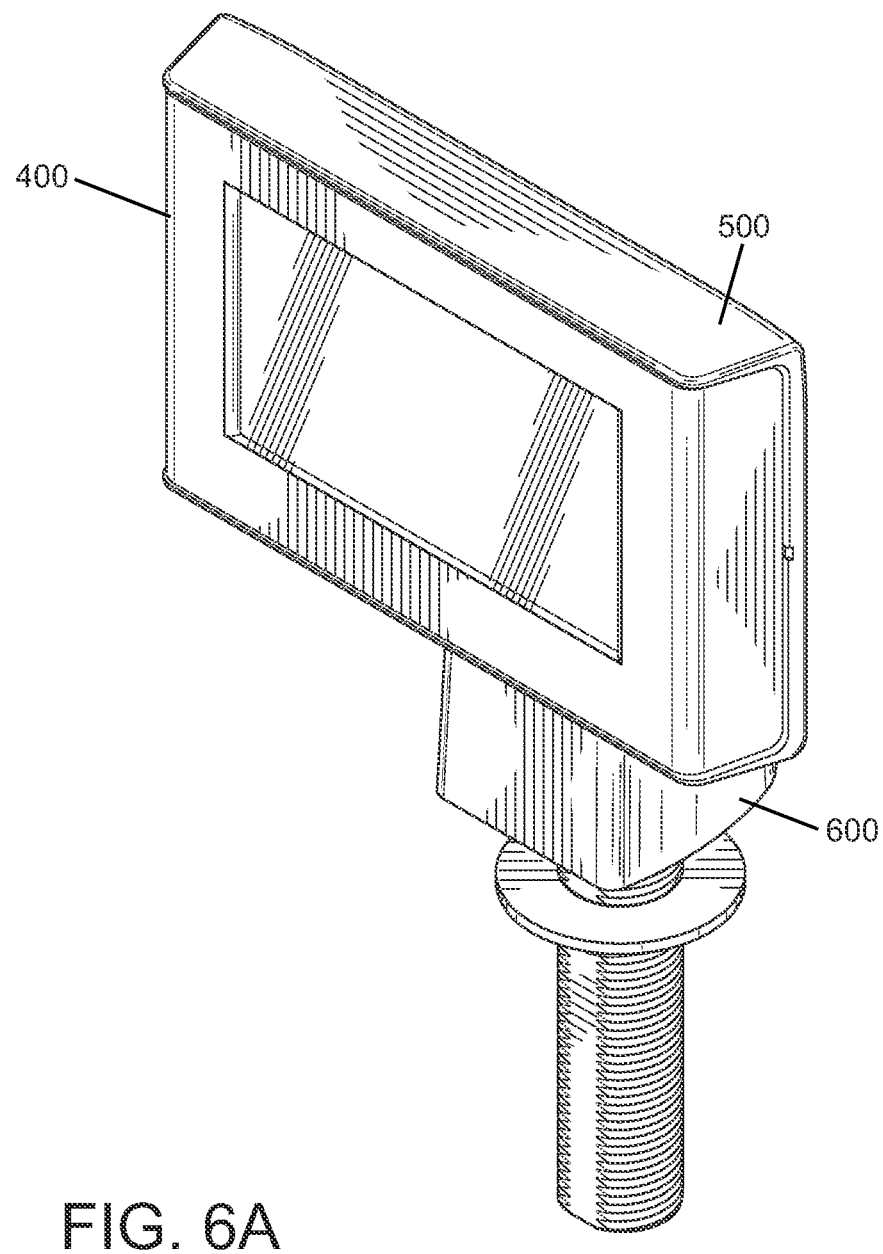
FIG. 6A is a perspective view of a mounting post to which a user interface device may be mounted according to an exemplary embodiment.
Figure 6B:
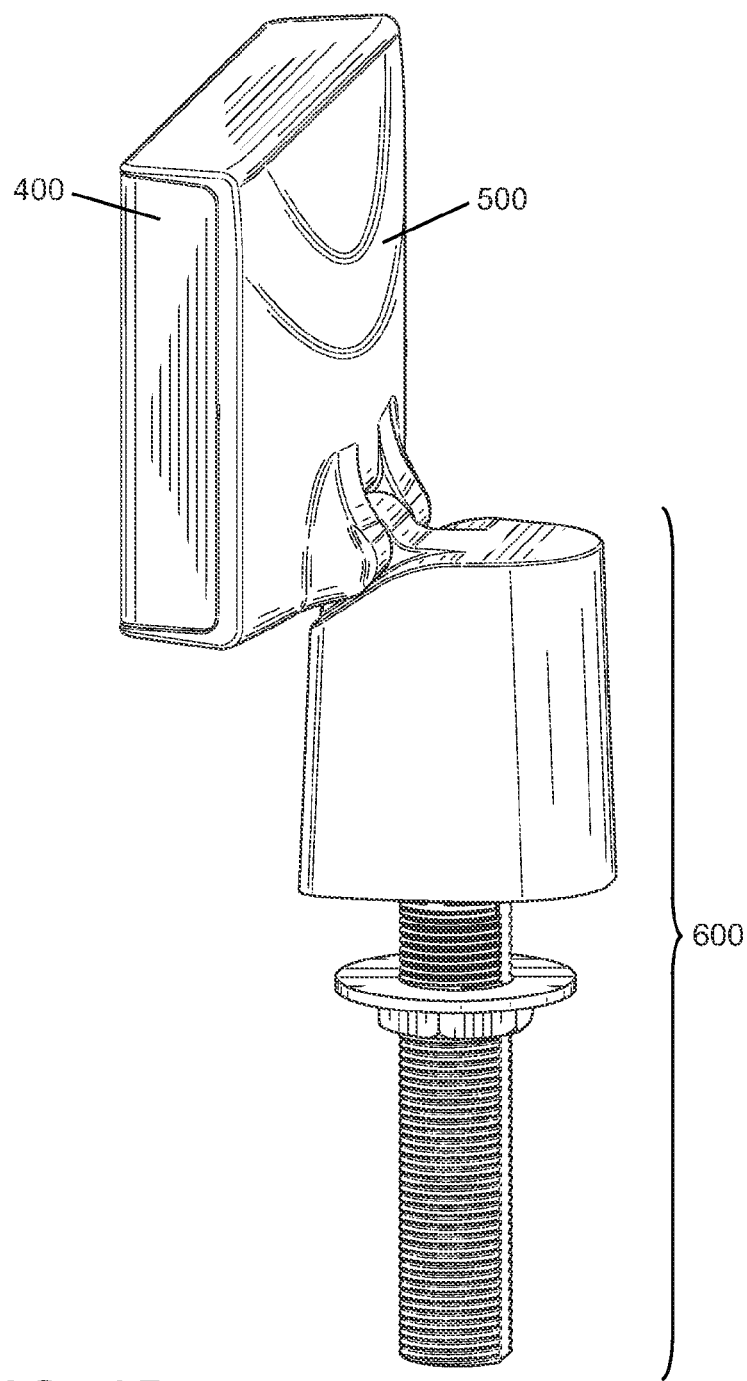
FIG. 6B is a side view of the mounting post shown in FIG. 6A according to an exemplary embodiment.

Referring now to FIGS. 6A and 6B, perspective and side views, respectively, of a mounting system to which user interface device 400 and mounting plate 500 may be coupled are shown according to an exemplary embodiment. Mounting system 600 may include a pole or rod configured to extend upward and a mounting adapter configured to mate to a corresponding adapter portion of mounting plate 500. The pole or rod may be partially hollow and may include an electrical cable configured to be electrically coupled to connector cable 406 of user interface device 400 and to electrically connect user interface device 400 to a control circuit for a bath or shower. Mounting system 600 may be configured to be height-adjustable to provide more comfortable use for users of differing heights. In some embodiments, mounting system 600 may be used to mount user interface device 400 on a side of a vibroacoustic bath tub. In some embodiments, a different mounting system, such as a wall mounting system configured to mount user interface device 400 against a wall near a bath tub or against a wall of a shower, may be used to mount user interface device 400 for use.

Referring now generally to FIGS. 7 through 20, several display images that may be provided on a touchscreen display device (e.g., user interface devices 340 and/or 400) are provided according to exemplary embodiments. The display images may be presented on the touchscreen display device, and user input in the way of user presses (e.g., finger presses) over certain portions of the displayed images may be used to receive user selections relating to the displayed images. The display images illustrated in FIGS. 7 through 20 may allow a user to manipulate user experience features of a vibroacoustic bathroom fixture, such as a bath tub.

Figure 7:
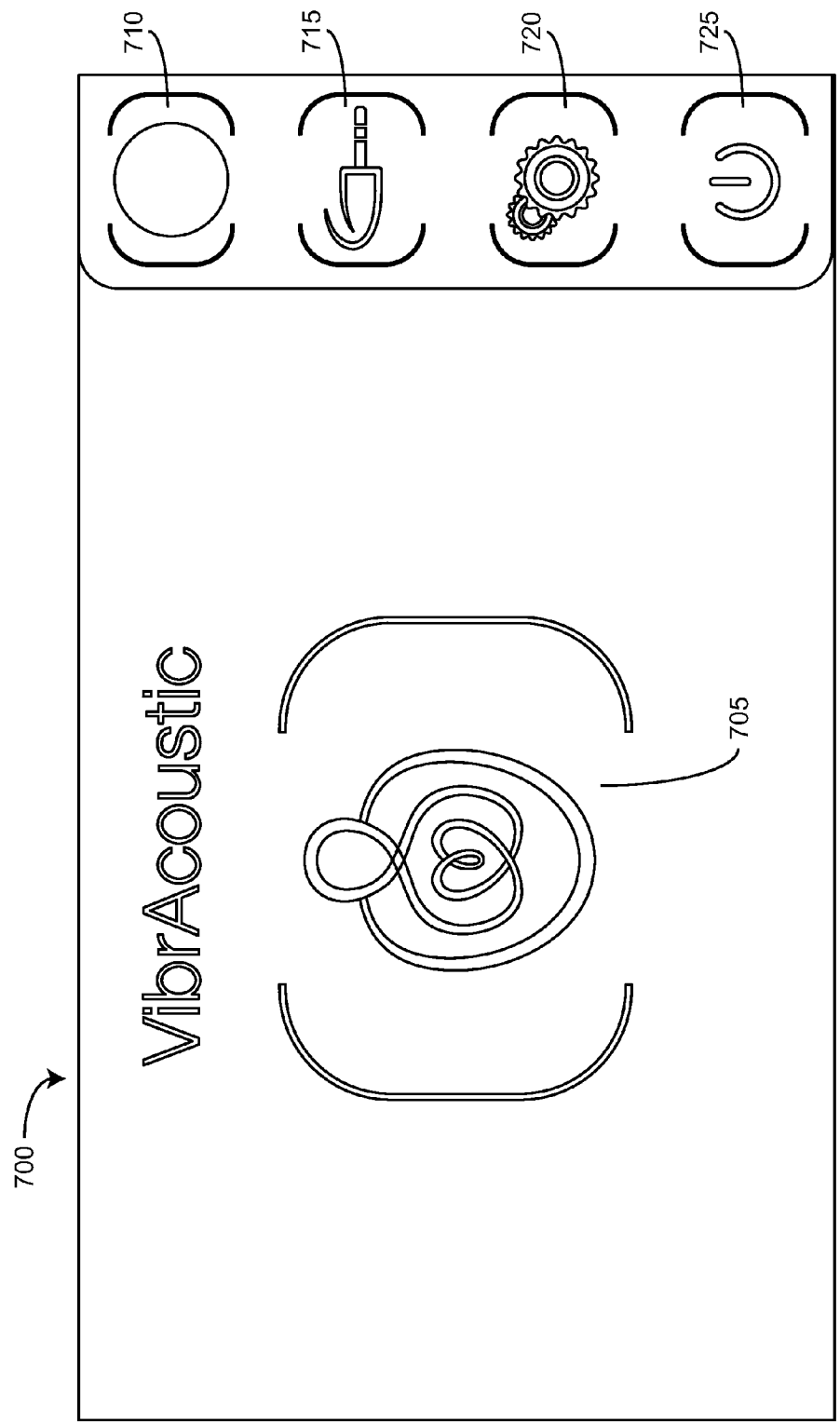
FIG. 7 is an illustration of a user interface display image according to an exemplary embodiment.

FIG. 7 illustrates a home screen 700 that includes a large experience icon 705 that is the primary selection on home screen 700. When a user selects experience icon 705, an experience selection screen may be shown that allows a user to select from one or more themes or music selections to be used in generating the aural and vibratory stimuli to be provided to the user. Home screen 700 also includes four secondary navigation options that appear as smaller icons on a right side of home screen 700, a chromatherapy icon 710, an auxiliary input icon 715, a settings icon 720, and a power off icon 725. When the user selects chromatherapy icon 710, a chromatherapy screen may be shown that enables a user to make selections that determine a color of one or more lighting units on or near the vibroacoustic fixture. When the user selects auxiliary input icon 715, the user is presented with an auxiliary input screen that may be used to provide audio signals from an external audio device (e.g., connected using an auxiliary audio jack, such as a mini-jack) to be used in generating the aural and vibratory stimuli to be provided to the user. When the user selects settings icon 720, the user is presented with a settings screen that may be used to modify settings of the user experience system. When the user selects power off icon 725, a control circuit to which the user interface device is connected may power off the user interface device as well as other devices of the user experience system, such as transducers and/or lighting units.

Figure 8:
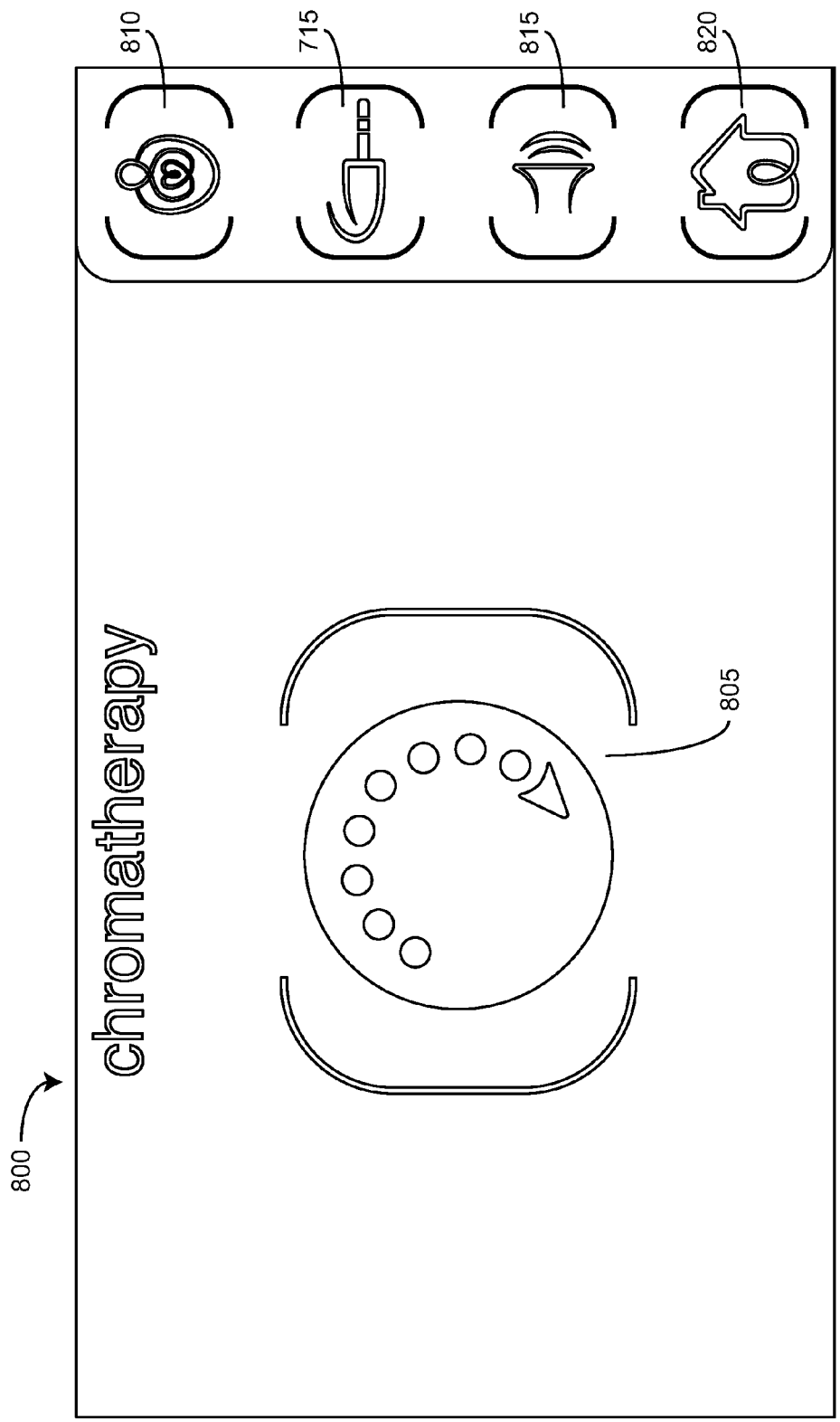
FIGS. 8 and 9 are illustrations of user interface display images that may be used to control a lighting system of a bath or shower fixture according to exemplary embodiments.
Figure 9:
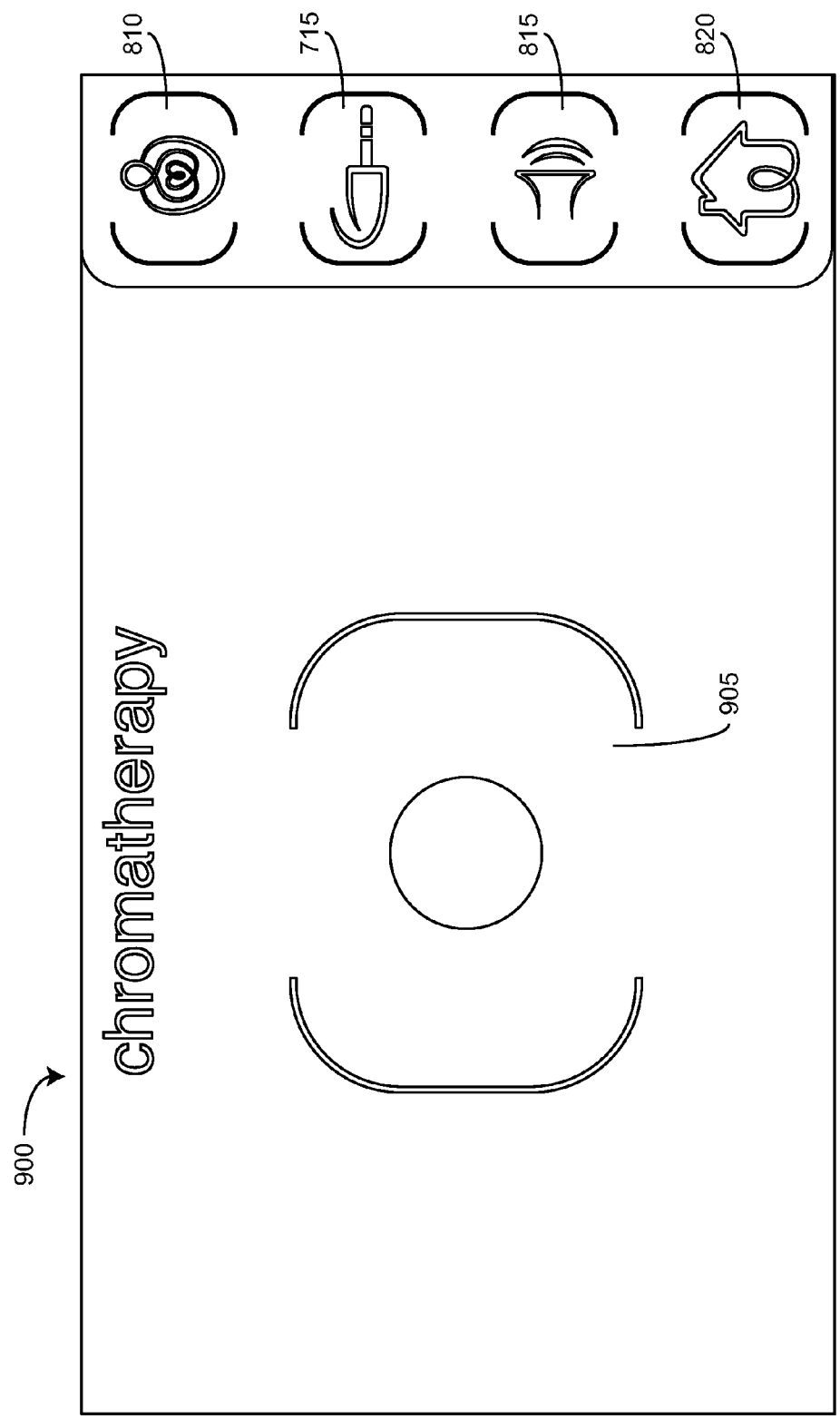

FIG. 8 illustrates a chromatherapy screen 800 that may be presented to a user upon selection of chromatherapy icon 710 on home screen 700. Chromatherapy screen 800 includes a chromatherapy control icon 805 that may be used to control a color mode for lighting units mounted on or near the vibroacoustic fixture. The illustrated chromatherapy control icon 805 that includes a dotted arrow may indicate that the chromatherapy system is currently set to a cycling mode in which the lighting units are continuously cycled through all available colors at predetermined intervals. When the user presses chromatherapy control icon 805, a second "paused" mode may be enabled in which a user may select a particular color to be emitted by the lighting units. For example, arrows may be presented to the sides of the icon for use in cycling through color options. When the user presses chromatherapy control icon 805 yet again when in the second "paused" mode, the chromatherapy function may be disabled and the lights may be turned off, as indicated by a chromatherapy disabled icon 905 shown in chromatherapy screen 900 of FIG. 9. Chromatherapy screens 800 and 900 also include secondary navigation options. The secondary navigation options include auxiliary input icon 715 as well as an experience navigation icon 810 that returns the user to an active audio/vibratory experience screen, an intensity icon 815 leading to a screen that may be used to adjust the intensity of audio and/or vibratory transducers of the vibroacoustic fixture, and home icon 820 that leads to home screen 700.

Figure 10:
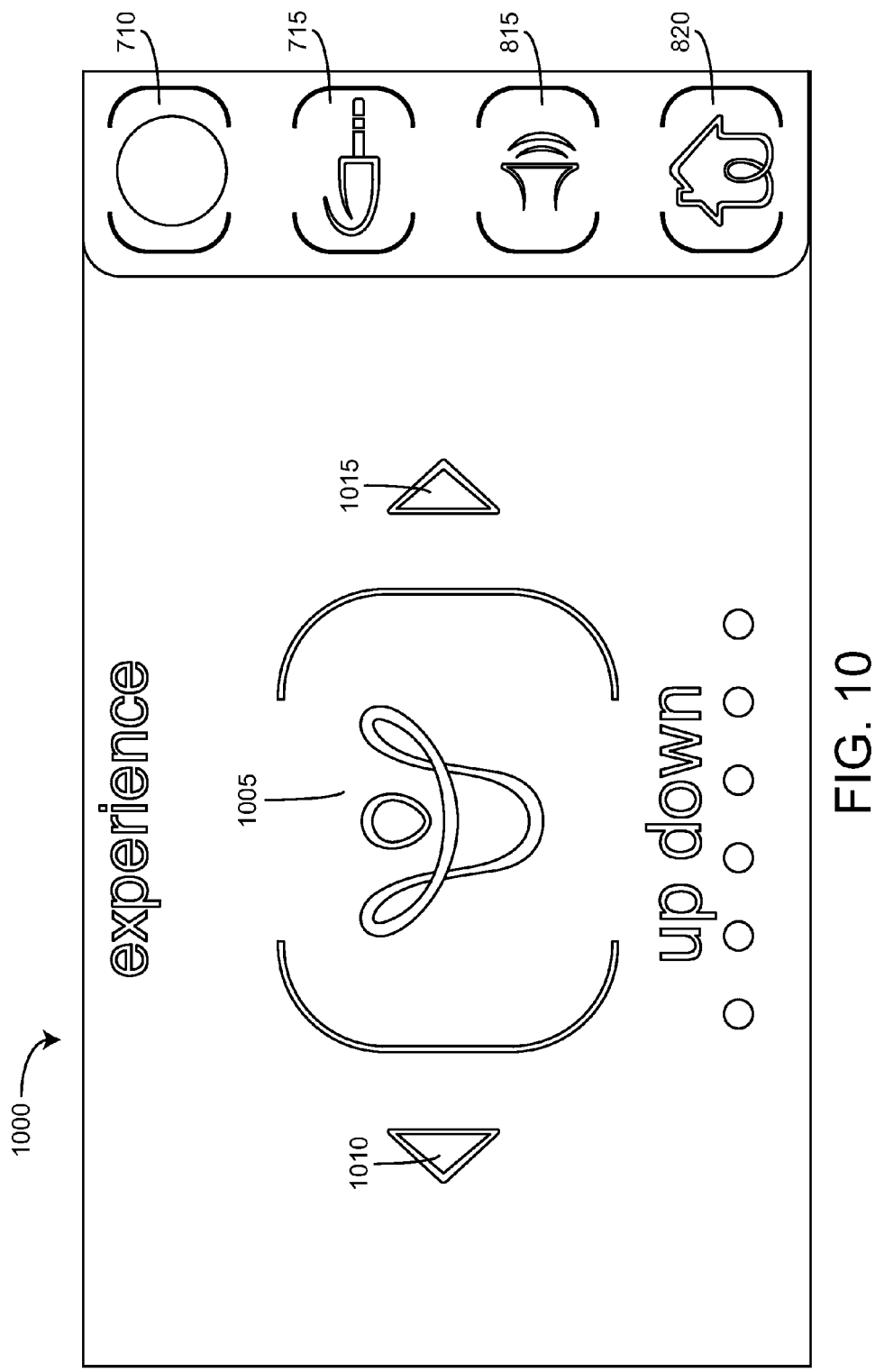
FIGS. 10-15 are illustrations of user interface display images that may be used to select a theme for use in generating aural and/or vibratory stimuli in a bath or shower fixture according to exemplary embodiments.
Figure 11:
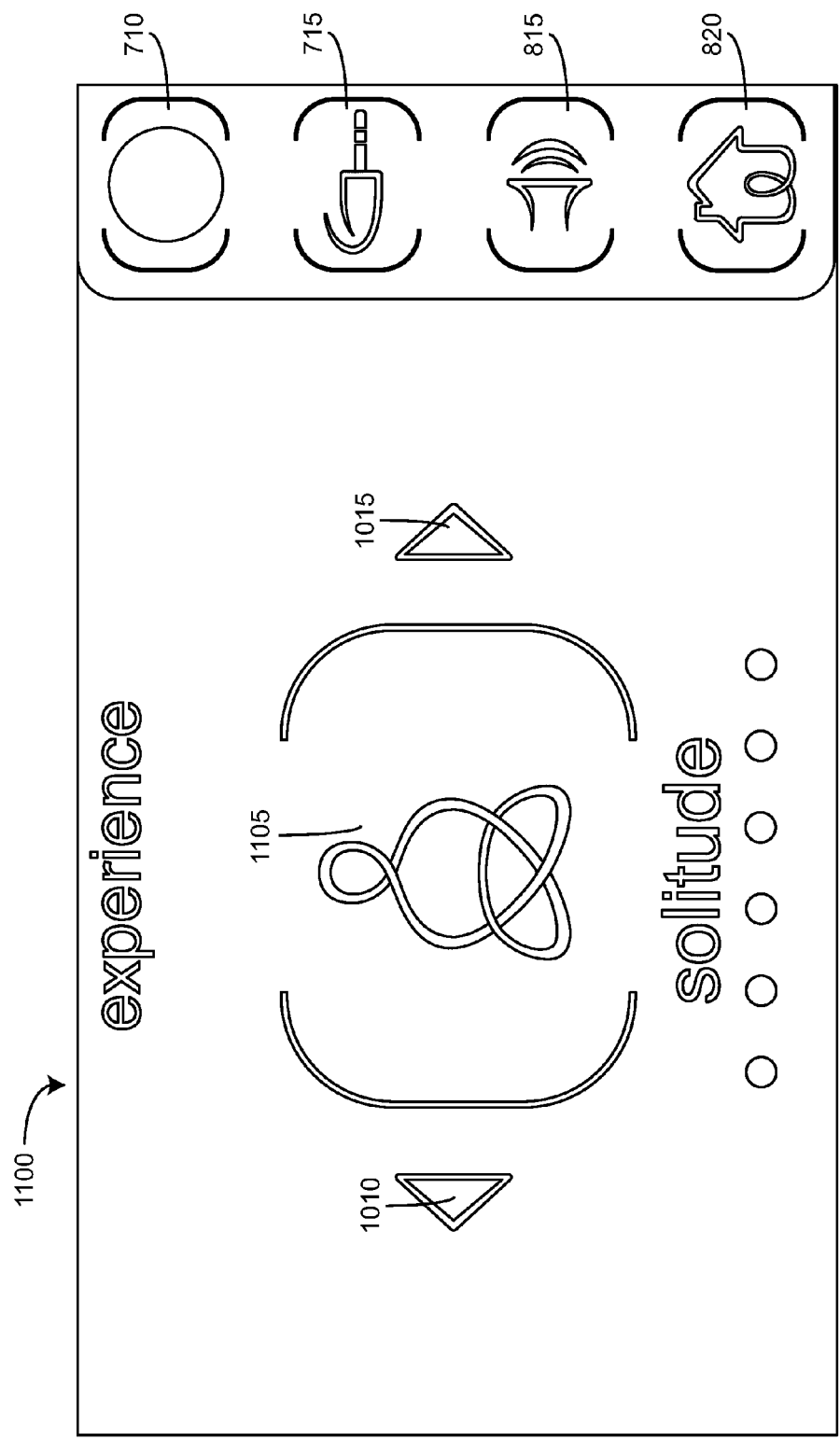
Figure 12:
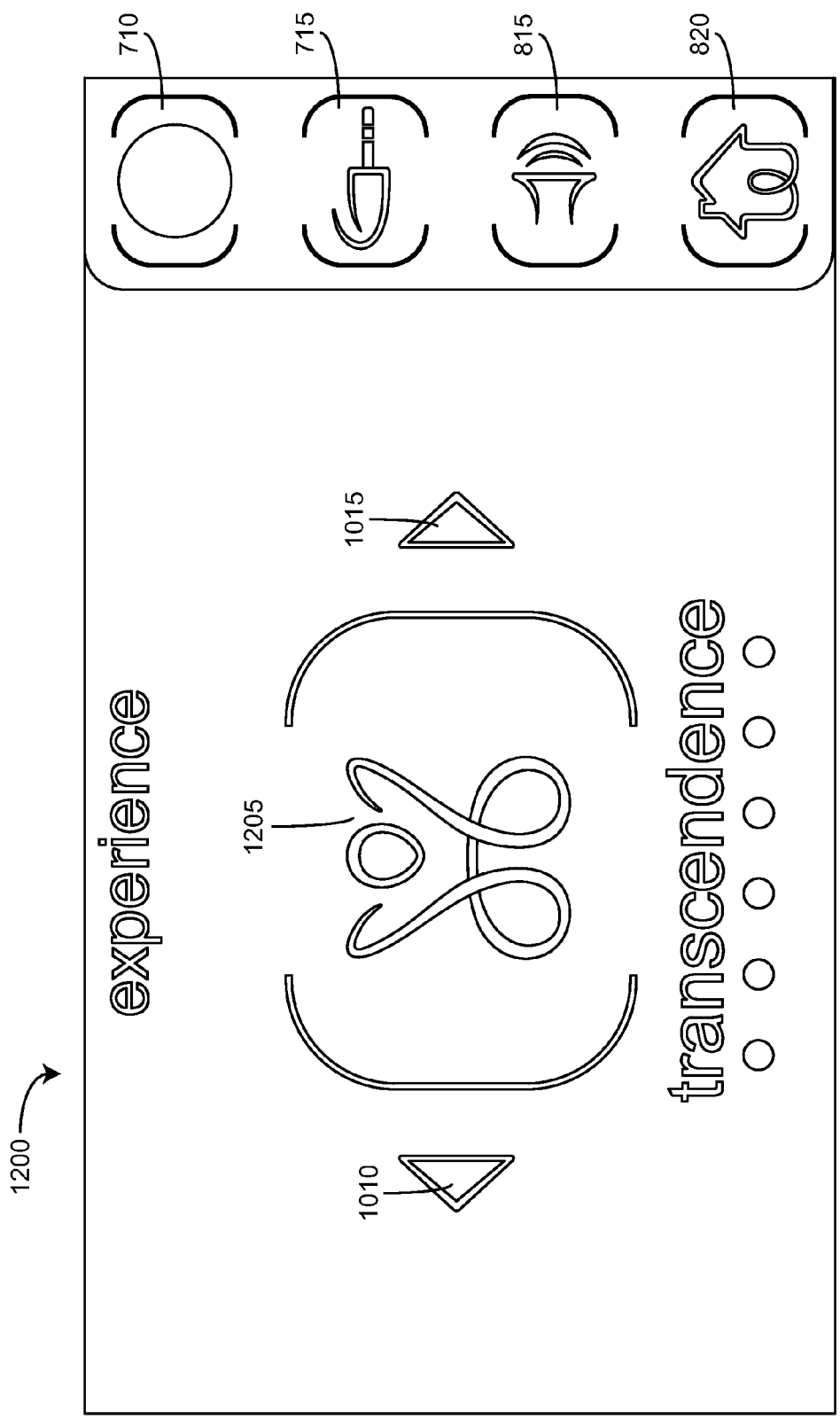
Figure 13:
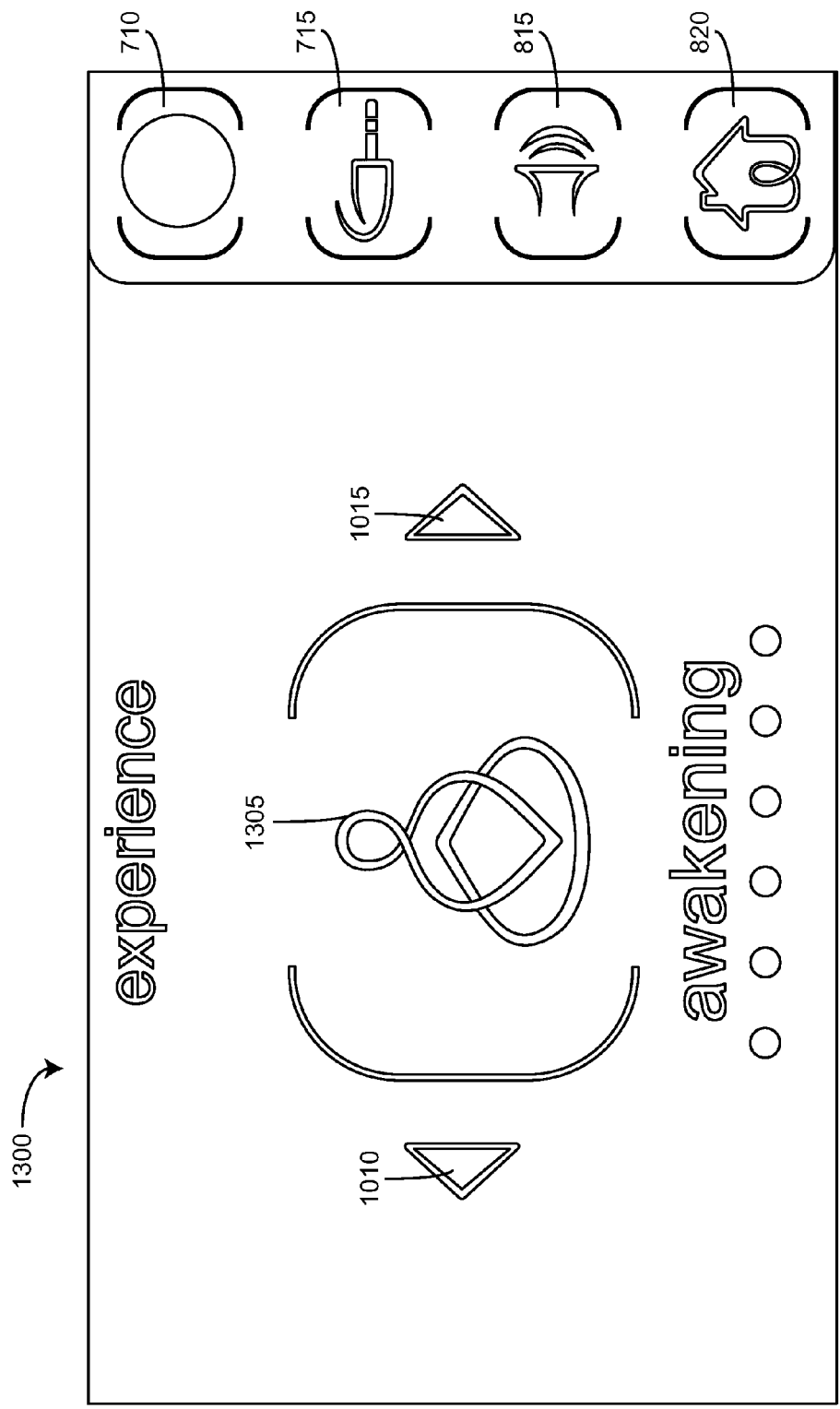
Figure 14:
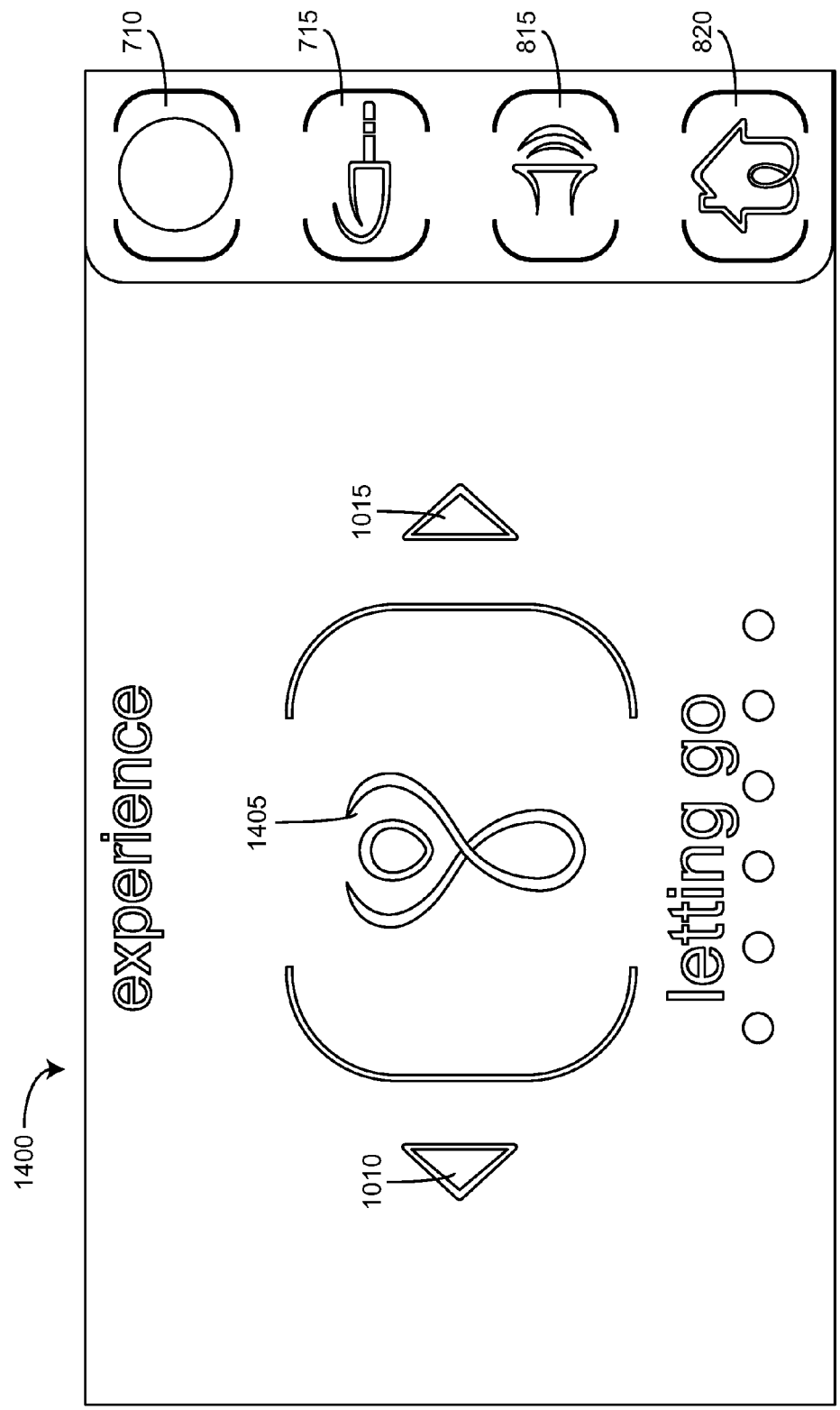
Figure 15:
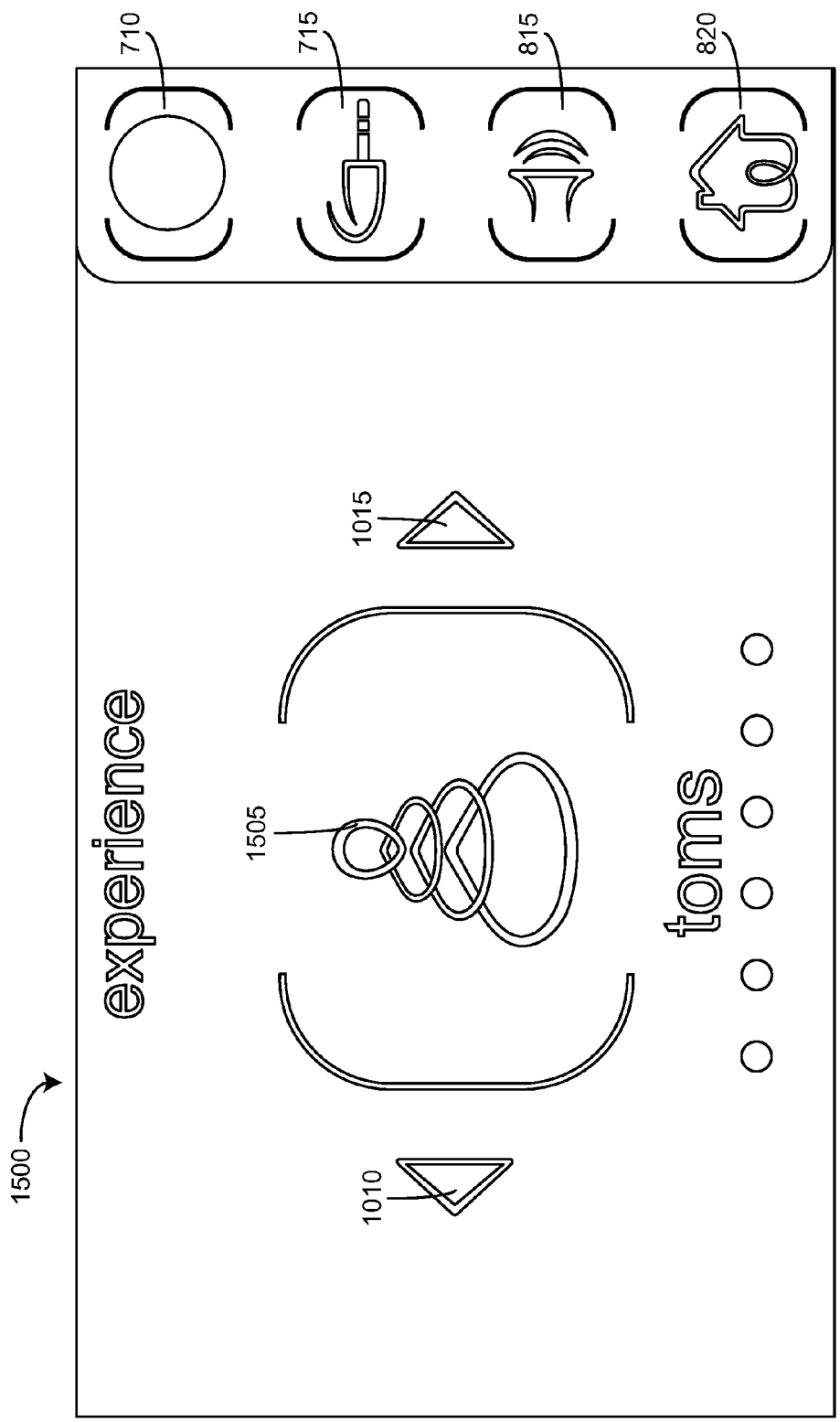

FIG. 10 illustrates an up down experience screen 1000 that may be displayed if a user selects experience icon 705 on home screen 700. An up down experience icon 1005 may be used to activate and deactivate aural and vibratory stimuli based upon an audio file associated with the up down experience theme. The up down experience theme may be associated with a particular pattern of aural and/or vibratory stimuli. The user may navigate to other experience themes by using directional keys 1010 and 1015. For example, the user may navigate to a solitude experience screen 1100, a transcendence experience screen 1200, an awakening experience theme 1300, a letting go experience theme 1400, and a toms experience theme 1500 (illustrated in FIGS. 11 through 15, respectively). Each of these experience screens may enable a user to activate and deactivate different experience themes that may correspond to different audio files to be used by a control system of the vibroacoustic fixture to generate aural and vibratory stimuli to be provided to the user.

Figure 16:
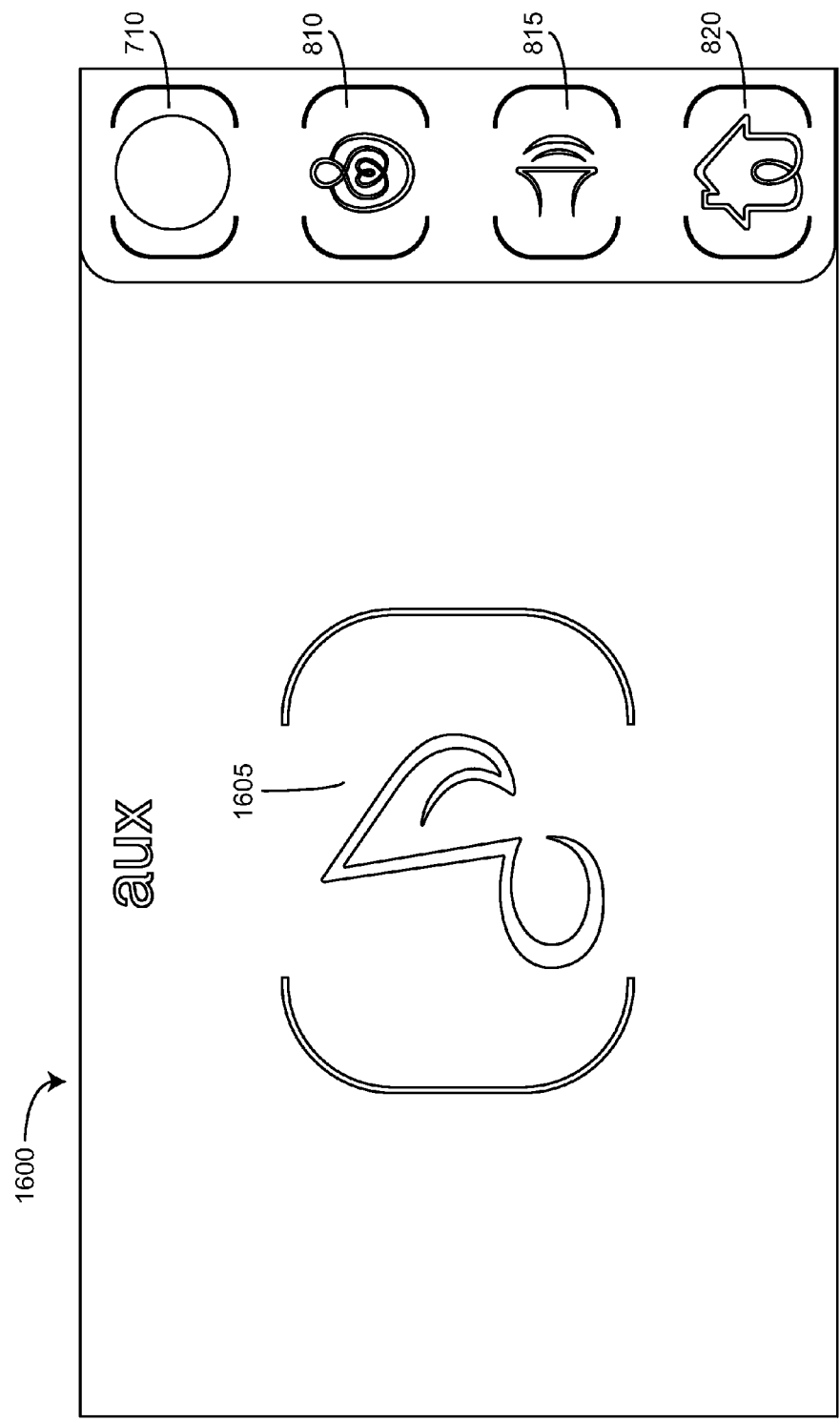
FIG. 16 is an illustration of a user interface display image that may be used to enable or disable an auxiliary audio input according to an exemplary embodiment.

FIG. 16 illustrates an auxiliary input screen 1600 that may be presented when a user selects auxiliary input icon 715 (e.g., on home screen 700). An auxiliary input icon 1605 may be selected to enable an auxiliary input port such that the user can connect an external media device and use the audio signal from the external media device to generate aural and vibratory stimuli to be provided to the user. If the user wishes to deactivate the auxiliary input port, the user may select auxiliary input icon 1605 to deactivate the port.

Figure 17:
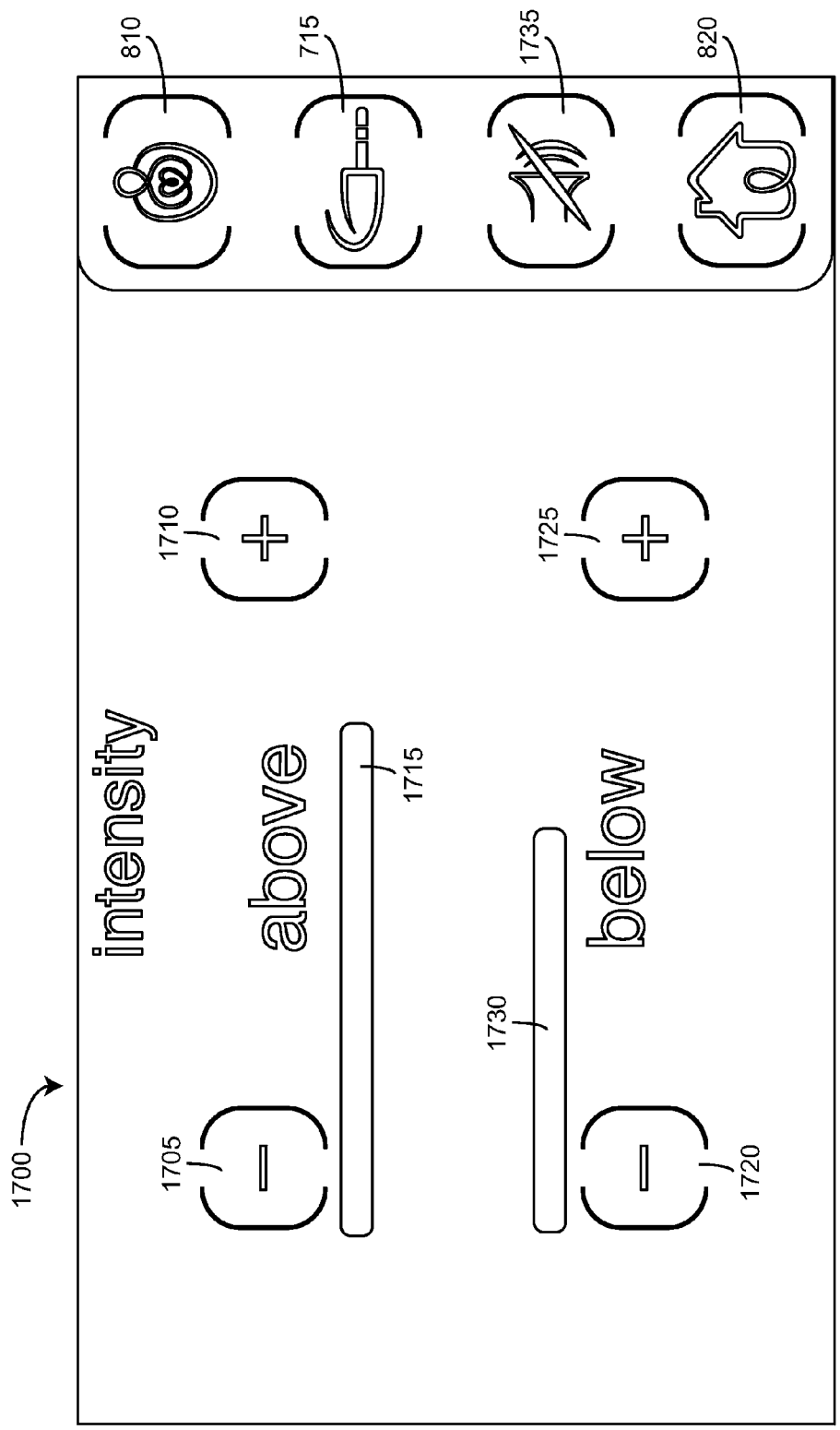
FIG. 17 is an illustration of a user interface display image that may be used to adjust one or more intensity levels of transducers of a bath or shower fixture according to an exemplary embodiment.

FIG. 17 illustrates an intensity screen 1700 that may be presented when a user selects intensity icon 815. Intensity screen 1700 may be used to adjust the output intensity or volume of audio and vibratory transducers of the vibroacoustic fixture. An upper intensity decrease icon 1705 may be used to reduce the intensity of the audio transducers, and an upper intensity increase icon 1710 may be used to increase the intensity of the audio transducers. An upper intensity status icon 1715 may provide an indication to the user of the current intensity of the audio transducers with respect to minimum and maximum intensity levels. For example, in the illustrated display screen, the audio transducers appear to currently be set at an intensity that is about two-thirds of the maximum intensity of the audio transducers. A lower intensity decrease icon 1720 may be used to reduce the intensity of the vibratory transducers, a lower intensity increase icon 1725 may be used to increase the intensity of the vibratory transducers, and a lower intensity status icon 1730 may indicate the current intensity of the vibratory transducers. In some embodiments, selecting a mute icon 1735 may cause the control system to stop driving aural and vibratory stimuli using the audio and vibratory transducers.

Figure 18:
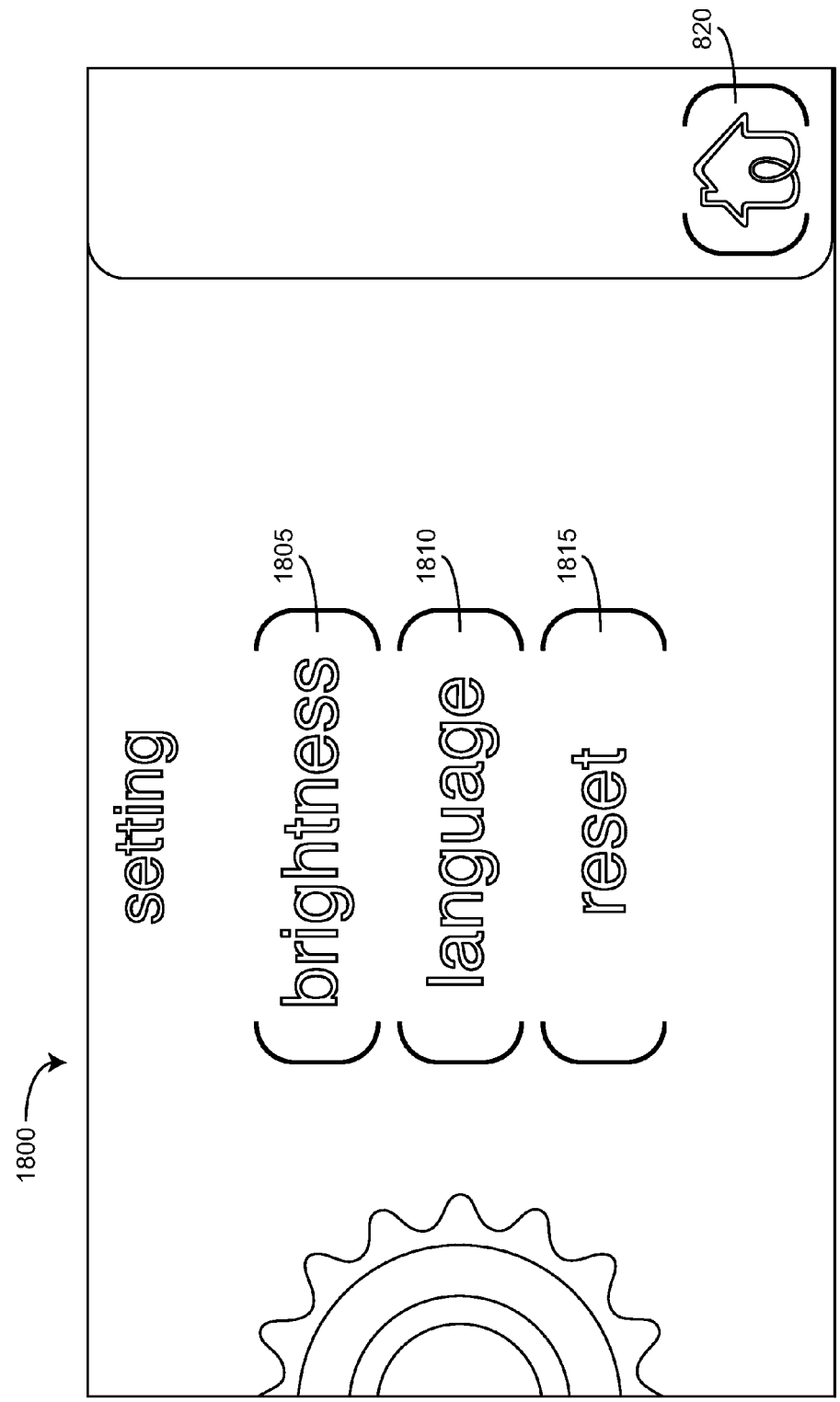
FIG. 18 is an illustration of a user interface display image that may be used to adjust settings associated with a bath or shower fixture according to an exemplary embodiment.

FIG. 18 illustrates a settings screen 1800 that may be presented when a user selects settings icon 720. A brightness icon 1805 may be selected to view a brightness options screen in which the intensity of the user interface display may be adjusted. A language icon 1810 may be selected to adjust a language to be used in display images presented on the user interface display. A reset button 1815 may be selected to restore the device to its original factory settings.

Figure 19:
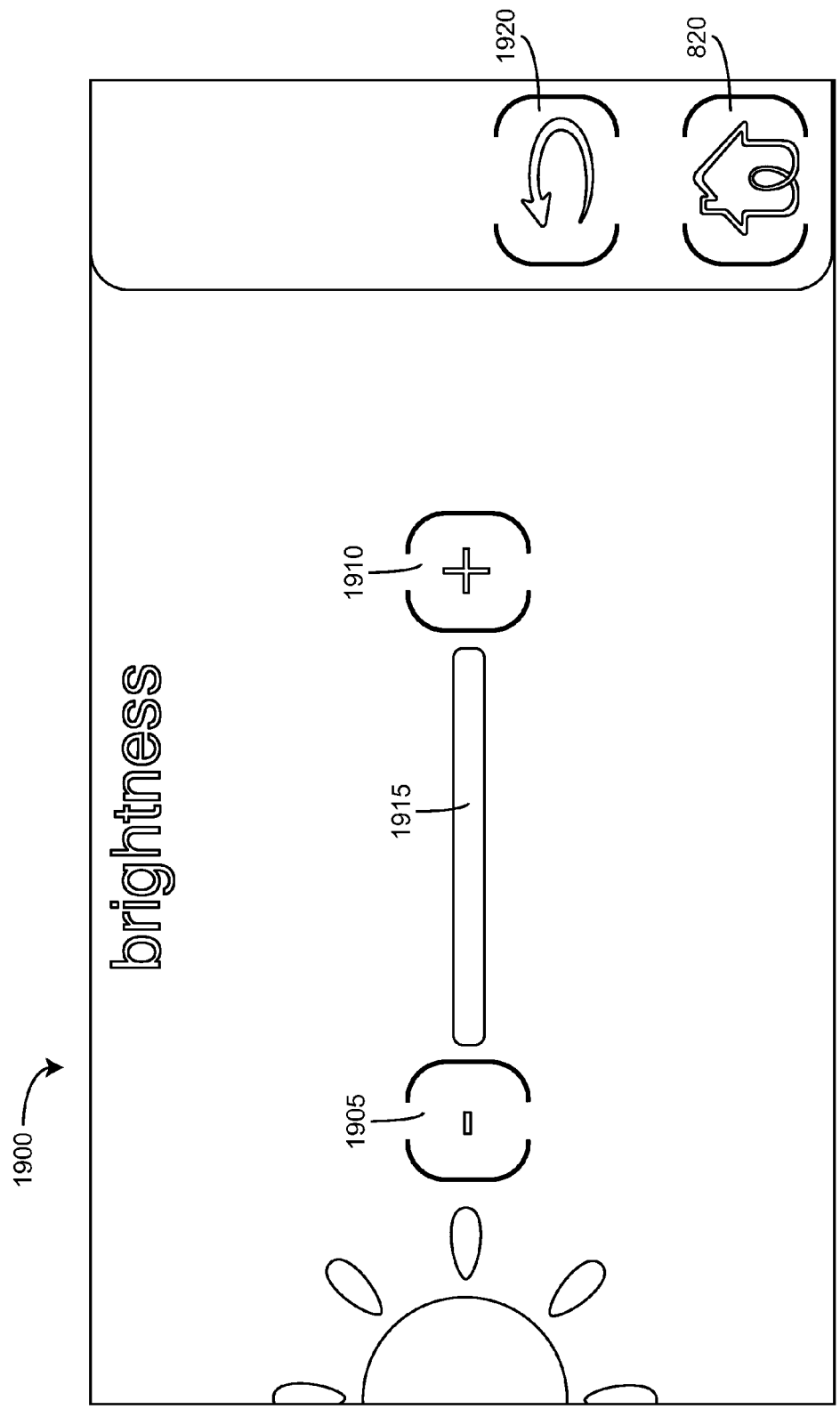
FIG. 19 is an illustration of a user interface display image that may be used to adjust a brightness of a user interface device according to an exemplary embodiment.

FIG. 19 illustrates a brightness screen 1900 that may be presented when a user selects brightness icon 1805. A decrease brightness icon 1905 may be used to decrease the brightness of the user interface display and an increase brightness icon 1910 may be used to increase the brightness of the user interface display. A brightness status indicator 1915 may indicate a current brightness setting for the user interface display with respect to a maximum and minimum brightness level of the display. A return icon 1920 may be used to return to settings screen 1800.

Figure 20:
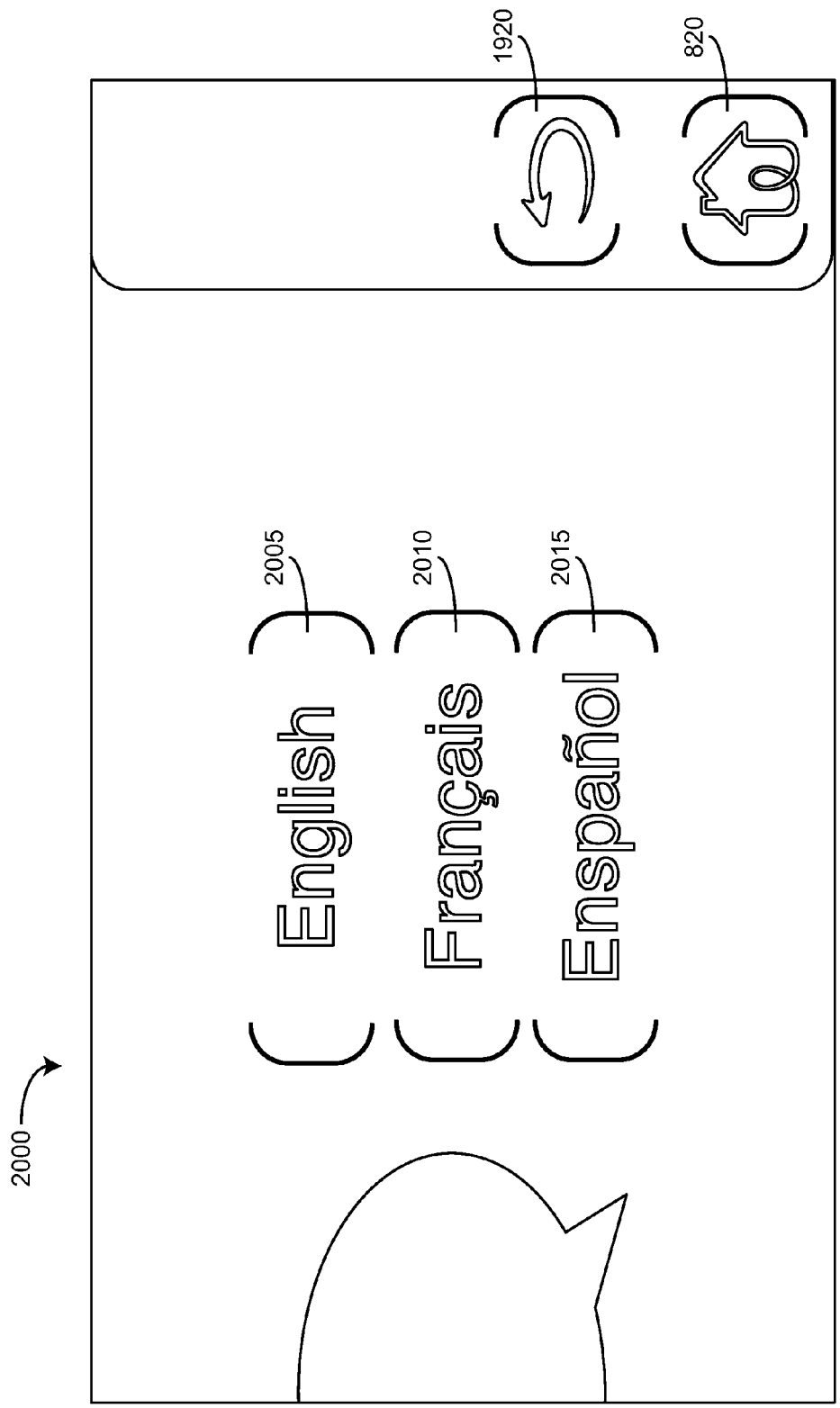
FIG. 20 is an illustration of a user interface display image that may be used to adjust a language to be used in providing display images on a user interface device according to an exemplary embodiment.

FIG. 20 illustrates a language screen 2000 that may be presented when a user selects language icon 1810. An English icon 2005 may be used to set display images to be presented on the user interface device to be provided in the English language. A French icon 2010 may be selected to set the display language to the French language, and a Spanish icon 2015 may be selected to set the display language to the Spanish language. In other embodiments, other languages may be supported by the user interface device.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media (e.g., tangible and/or non-transitory) for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, flash memory, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A water system comprising:
    a reservoir configured to contain water and comprising a wall, a first axis of symmetry substantially parallel to and equidistant from sides of the reservoir, and a second axis of symmetry substantially parallel to and equidistant from ends of the reservoir; and
    four vibratory transducers mounted against the wall of the reservoir, the four vibratory transducers being configured to receive an input signal and to generate vibrations within water contained in the reservoir by vibrating the wall of the reservoir,
    wherein the four vibratory transducers are mounted in an asymmetrical configuration with respect to both the first axis of symmetry and the second axis of symmetry such that, when the wall is partitioned into four sections, only a single vibratory transducer is mounted against each section of the wall and no other vibratory transducers are mounted against the wall, wherein the asymmetrical configuration reduces an interference and cancelling effect between vibratory waves produced by each of the vibratory transducers.

2. The water system of claim 1, wherein the reservoir has a substantially rectangular shape, wherein none of the four transducers are intersected by the first axis of symmetry or the second axis of symmetry.

3. The water system of claim 2, wherein:
    a first vibratory transducer is mounted against a first side of the reservoir,
    a second vibratory transducer is mounted against a second side of the reservoir,
    a third vibratory transducer is mounted against a first end of the reservoir,
    a fourth vibratory transducer is mounted against a second end of the reservoir,
    the first vibratory transducer and the second vibratory transducer are laterally offset from the second axis by a same first distance, and
    the third vibratory transducer and the fourth vibratory transducer are laterally offset from the first axis by a same second distance.

4. The water system of claim 3, wherein the first distance is larger than the second distance.

5. The water system of claim 1, wherein the reservoir has a substantially ovular shape with the first axis of symmetry being a major axis and the second axis of symmetry being a minor axis, and wherein none of the four vibratory transducers are intersected by the major axis or the minor axis.

6. The water system of claim 5, wherein a first vibratory transducer and a second vibratory transducer are laterally offset from the major axis by a same first distance, and wherein a third vibratory transducer and a fourth vibratory transducer are laterally offset from the minor axis by a same second distance.

7. The water system of claim 6, wherein the second distance is larger than the first distance.

8. The water system of claim 5, wherein the reservoir has a substantially elliptical shape, wherein a first vibratory transducer and a second vibratory transducer are laterally offset from the major axis by a same first distance, and wherein a third vibratory transducer and a fourth vibratory transducer are laterally offset from the minor axis by a same second distance.

9. The water system of claim 1, wherein the bathing system further comprises:
    a set of two or more audio transducers mounted on the reservoir at positions above a maximum water level of the reservoir and configured to receive an input signal and generate an aural output using the reservoir; and
    a control circuit configured to generate signals to drive both the set of vibratory transducers and the set of audio transducers based on a single audio input file, wherein the control circuit coordinates operation of the vibratory transducers and the audio transducers to produce a vibroacoustic experience in which the vibrations within the water and the aural output are coordinated.

10. The water system of claim 9, wherein the control circuit is configured to generate a first channel output signal configured to drive both a first subset of the vibratory transducers and a first subset of the audio transducers, and wherein the control circuit is configured to generate a second channel output signal configured to drive both a second subset of the vibratory transducers and a second subset of the audio transducers.

11. A bathing system comprising:
    a tub configured to contain water and comprising a wall, a first axis of symmetry substantially parallel to and equidistant from sides of the tub, and a second axis of symmetry substantially parallel to and equidistant from ends of the tub;
    four vibratory transducers mounted against the wall of the tub, the four transducers being configured to receive an input signal and to generate vibrations within water contained in the tub by vibrating the wall of the tub;
    a plurality of audio transducers mounted on the tub at positions above a maximum water level of the tub and configured to receive an input signal and generate an aural output using the tub; and
    a control circuit configured to generate signals to drive both the vibratory transducers and the audio transducers, wherein the control circuit coordinates operation of the vibratory transducers and the audio transducers to produce a vibroacoustic experience in which the vibrations within the water and the aural output are coordinated, wherein the four vibratory transducers are mounted in an asymmetrical configuration with respect to both the first axis of symmetry and the second axis of symmetry such that, when the wall is partitioned into four sections, only a single vibratory transducer is mounted against each section of the wall and no other vibratory transducers are mounted against the wall, wherein the asymmetrical configuration reduces an interference and cancelling effect between vibratory waves produced by each of the vibratory transducers.

12. The bathing system of claim 11, wherein the tub has a substantially rectangular shape, wherein none of the four vibratory transducers are intersected by the first axis of symmetry or the second axis of symmetry.

13. The bathing system of claim 12, wherein:
a first vibratory transducer is mounted against a first side of the tub,
a second vibratory transducer is mounted against a second side of the tub,
a third vibratory transducer is mounted against a first end of the tub,
a fourth vibratory transducer is mounted against a second end of the tub,
the first vibratory transducer and the second vibratory transducer are laterally offset from the second axis by a same first distance, and
the third vibratory transducer and the fourth vibratory transducer are laterally offset from the first axis by a same second distance.

14. The bathing system of claim 13, wherein the first distance is larger than the second distance.

15. The bathing system of claim 11, wherein the tub has a substantially ovular shape with the first axis of symmetry being a major axis and the second axis of symmetry being a minor axis, and wherein none of the four vibratory transducers are intersected by the major axis or the minor axis.

16. The bathing system of claim 15, wherein a first vibratory transducer and a second vibratory transducer are laterally offset from the major axis by a same first distance, and wherein a third vibratory transducer and a fourth vibratory transducer are laterally offset from the minor axis by a same second distance.

17. The bathing system of claim 16, wherein the second distance is larger than the first distance.

18. The bathing system of claim 15, wherein the tub has a substantially elliptical shape, wherein a first vibratory transducer and a second vibratory transducer are laterally offset from the major axis by a same first distance, and wherein a third vibratory transducer and a fourth vibratory transducer are laterally offset from the minor axis by a same second distance.

19. The bathing system of claim 11, wherein the control circuit is configured to generate the signals to drive both the vibratory transducers and the audio transducers based on a single audio input file, wherein the control circuit is configured to generate a first channel output signal configured to drive both a first subset of the vibratory transducers and a first subset of the audio transducers, and wherein the control circuit is configured to generate a second channel output signal configured to drive both a second subset of the vibratory transducers and a second subset of the audio transducers, each subset comprising one or more transducers.

20. The bathing system of claim 11, wherein the vibratory transducers and the audio transducers are a same type of transducer.

21. A water system consisting of:
a reservoir configured to contain water and comprising a wall, a first axis of symmetry substantially parallel to and equidistant from sides of the reservoir, and a second axis of symmetry substantially parallel to and equidistant from ends of the reservoir; and
four transducers mounted against the wall of the reservoir, the four transducers being configured to receive an input signal and to generate vibrations within water contained in the reservoir by vibrating the wall of the reservoir,
wherein the four transducers are mounted in an asymmetrical configuration with respect to both the first axis of symmetry and the second axis of symmetry such that, when the wall is partitioned into four sections, only a single transducer is mounted against each section of the wall and no other transducers are mounted against the wall, wherein the asymmetrical configuration reduces an interference and cancelling effect between vibratory waves produced by each of the four transducers.

* * * * *